US008933935B2

(12) United States Patent
Yang et al.

(10) Patent No.: US 8,933,935 B2
(45) Date of Patent: Jan. 13, 2015

(54) METHOD OF RENDERING AND MANIPULATING ANATOMICAL IMAGES ON MOBILE COMPUTING DEVICE

(71) Applicants: Victor Yang, Toronto (CA); Beau Anthony Standish, Toronto (CA); Richard Jeffrey Rzeszutek, Toronto (CA); Michael Leung, Markham (CA); Adrian Mariampillai, Toronto (CA); Dimitrios Androutsos, Toronto (CA)

(72) Inventors: Victor Yang, Toronto (CA); Beau Anthony Standish, Toronto (CA); Richard Jeffrey Rzeszutek, Toronto (CA); Michael Leung, Markham (CA); Adrian Mariampillai, Toronto (CA); Dimitrios Androutsos, Toronto (CA)

(73) Assignee: 7D Surgical Inc., Toronto (CA)

( * ) Notice: Subject to any disclaimer, the term of this patent is extended or adjusted under 35 U.S.C. 154(b) by 256 days.

(21) Appl. No.: 13/675,196

(22) Filed: Nov. 13, 2012

(65) Prior Publication Data

US 2013/0135312 A1    May 30, 2013

Related U.S. Application Data

(60) Provisional application No. 61/558,039, filed on Nov. 10, 2011.

(51) Int. Cl.
*G06T 15/10* (2011.01)
*A61B 19/00* (2006.01)
*G06T 3/00* (2006.01)

(52) U.S. Cl.
CPC ............... *A61B 19/50* (2013.01); *G06T 3/0006* (2013.01); *A61B 19/56* (2013.01); *A61B 2019/501* (2013.01)

USPC .......................................................... 345/427

(58) Field of Classification Search
CPC . A61B 19/50; A61B 2019/501; G06T 3/0006
See application file for complete search history.

(56) References Cited

U.S. PATENT DOCUMENTS

| 2007/0032720 | A1 | 2/2007 | Koivukangas et al. | |
| 2007/0238981 | A1* | 10/2007 | Zhu et al. | 600/424 |
| 2008/0071142 | A1* | 3/2008 | Gattani et al. | 600/117 |
| 2008/0194946 | A1* | 8/2008 | Summers et al. | 600/425 |
| 2009/0021475 | A1 | 1/2009 | Steinle et al. | |
| 2010/0171691 | A1 | 7/2010 | Cook et al. | |
| 2011/0157168 | A1 | 6/2011 | Bennett et al. | |
| 2011/0160738 | A1* | 6/2011 | McIntosh et al. | 606/102 |
| 2012/0016269 | A1* | 1/2012 | Moctezuma de la Barrera | 600/595 |
| 2012/0101388 | A1* | 4/2012 | Tripathi | 600/459 |

FOREIGN PATENT DOCUMENTS

WO    2011/058948    5/2011

* cited by examiner

*Primary Examiner* — James A Thompson
*Assistant Examiner* — Xilin Guo
(74) *Attorney, Agent, or Firm* — Hill & Schumacher

(57) ABSTRACT

Methods are provided for rendering an image of an anatomical object on a display of a mobile computing device. Sensors of the mobile computing device are interrogated to determine an orientation, or a change in orientation, of the computing device. Transformations are determined for rotating and positioning the image of the anatomical object such that the image appears to be stationary after a change in the orientation of the mobile computing device. Additional image data associated with a surgical tool or a surgical plan may also be rendered on the device for planning and/or training simulations.

21 Claims, 24 Drawing Sheets

METHOD OF RENDERING AND MANIPULATING ANATOMICAL IMAGES ON MOBILE COMPUTING DEVICE

CROSS-REFERENCE TO RELATED APPLICATION

This application claims priority to U.S. Provisional Application No. 61/558,039, titled "METHOD OF RENDERING AND MANIPULATING ANATOMICAL IMAGES ON MOBILE COMPUTING DEVICE" and filed on Nov. 10, 2011, the entire contents of which are incorporated herein by reference.

BACKGROUND

Simulation is a useful tool in medical training and in preparation for medical procedures. For example, simulation can be used for training students in a professional discipline on the different techniques related to that discipline. Similarly, simulation can also be used to assist experienced professionals in planning or testing out different scenarios that would either be infeasible or outright dangerous to do in the field.

The use of simulations by professionals in the medical field is generally restricted to training medical students and planning complex procedures. The advantage of simulations is that they allow the surgeon to practice and plan techniques, such as pedicle screw placement for spinal surgery, in advance of the actual procedure, thereby reducing risk to the patient. Due to recent advances in imaging technology, accurate three-dimensional models of the anatomy can be presented by the simulator, to the surgeon. The surgeon is then able to utilize pre-defined anatomical atlases or actual patient data for planning the surgical procedure.

A disadvantage to current medical simulation systems is the lack of natural interaction with the simulated anatomical structure. Existing simulation software often consists of nothing more than a standard desktop software package, whereby all interactions are done through a keyboard and/or mouse. More complex simulation systems are available that have the ability to accurately simulate one particular surgical technique for training and planning. However these systems require specialized and costly hardware, and lack the flexibility of a purely software solution.

SUMMARY

Methods are provided for rendering and manipulating an image of an anatomical object on a display of a mobile computing device. Sensors of the mobile computing device are interrogated to determine an orientation, or a change in orientation, of the computing device. Transformations are determined for rotating and positioning the image of the anatomical object such that the image appears to be stationary after a change in the orientation of the mobile computing device. Additional image data associated with a surgical tool or a surgical plan may also be rendered on the device for planning and/or training simulations.

In one embodiment, the user is able to interact with the model by placing screws on the surface of the model. This process is intended to simulate the process that a surgeon would go through when performing a surgery. Through a number of different interaction modalities, such as, but not limited to, touch, gestures and motion, the user can determine both the entry point and trajectory of the screw for implantation. The user is also able to select a number of different screws, where the geometry of the screw can be optimized for the ideal implantation of the mobile computing device. Example implementations are provided to describe how the present embodiments can be used for surgical planning and training.

Accordingly, in one aspect, there is provided a computer implemented method of dynamically displaying an anatomical object on a mobile computing device, the mobile computing device including sensors for determining an orientation of the mobile computing device and a display for displaying the anatomical object, the method comprising the steps of: a) obtaining three-dimensional image data associated with the anatomical object; b) determining a virtual camera vector defining a distance between a virtual camera and the anatomical object upon rendering of the anatomical object; c) determining a reference vector associated with the anatomical object, such that when rendering the anatomical object on the display, the reference vector is aligned with a gravity vector when the mobile computing device is oriented in a reference orientation; d) interrogating the sensors of the mobile computing device and determining an orientation of the mobile computing device; e) determining a transformation such that the reference vector is aligned with the gravity vector, and such that the anatomical object is perceived as residing within the display at a location corresponding to the virtual camera vector; f) applying the transformation to three-dimensional image data and obtaining transformed three-dimensional image data such that when rendered on the display, the anatomical object image appears to be stationary after a change in the orientation of the mobile computing device; and g) rendering an image of the anatomical object on the display of the mobile computing device according to the transformed three-dimensional image data.

In another aspect, there is provided a computer implemented method of dynamically displaying an anatomical object on a mobile computing device, the mobile computing device including sensors for determining an orientation of the mobile computing device and a display for displaying the anatomical object, the method comprising the steps of: a) obtaining three-dimensional image data associated with the anatomical object; b) interrogating the sensors of the mobile computing device and determining a change in an orientation of the mobile computing device; c) rendering an image of the anatomical object on the display, such that the anatomical object image appears to be stationary after the change in the orientation of the mobile computing device.

In another aspect, there is provided a computer-readable storage medium comprising instructions for dynamically displaying an anatomical object on a mobile computing device, the mobile computing device including sensors for determining an orientation of the mobile computing device and a display for displaying the anatomical object, wherein execution of the instructions by one or more processors causes the one or more processors to carry out the steps of: a) obtaining three-dimensional image data associated with the anatomical object; b) determining a virtual camera vector defining a distance between a virtual camera and the anatomical object upon rendering of the anatomical object; c) determining a reference vector associated with the anatomical object, such that when rendering the anatomical object on the display, the reference vector is aligned with a gravity vector when the mobile computing device is oriented in a reference orientation; d) interrogating the sensors of the mobile computing device and determining an orientation of the mobile computing device; e) determining a transformation such that the reference vector is aligned with the gravity vector, and such that the anatomical object is perceived as residing within the display at a location corresponding to the virtual camera vector; f) applying the transformation to three-dimensional image data and obtaining transformed three-dimensional image data such that when rendered on the display, the anatomical object image appears to be stationary after a change in the orientation of the mobile computing device; and g) rendering an image of the anatomical object on the display of the mobile computing device according to the transformed three-dimensional image data.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which.

DETAILED DESCRIPTION

Figure 1:
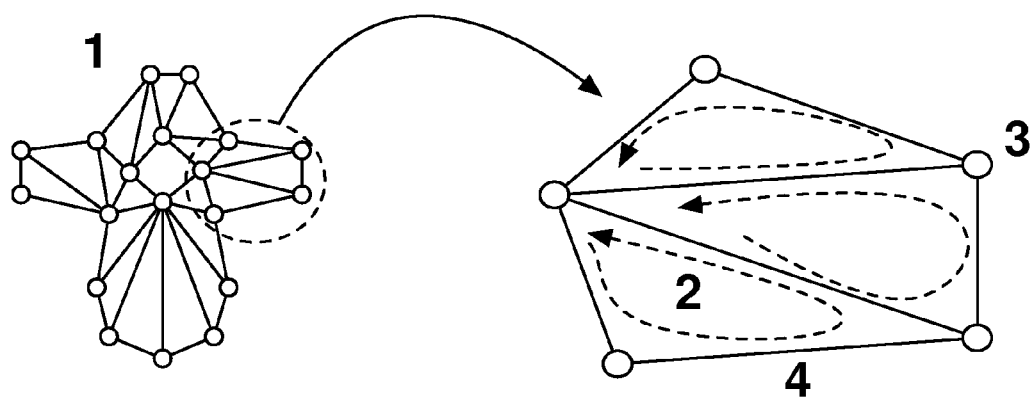
FIG. 1 is an illustration of mesh-based object representation and how meshes are represented on a computing mobile computing device.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately", when used in conjunction with ranges of dimensions of particles, compositions of mixtures or other physical properties or characteristics, are meant to cover slight variations that may exist in the upper and lower limits of the ranges of dimensions so as to not exclude embodiments where on average most of the dimensions are satisfied but where statistically dimensions may exist outside this region. It is not the intention to exclude embodiments such as these from the present disclosure. The following terms used in this description have the following meanings:

As used herein, the term "orientation" refers to the angular position of a mobile computing device with respect to a global coordinate frame.

As used herein, the term "anatomical" refers to any portion of a living entity. For example, "anatomical" may refer to a portion of the human anatomy, where portion of the human anatomy may include a portion of a tissue, organ, and/or cavity.

As used herein, the term "transformation" refers to a linear or nonlinear mapping of $R^3 \rightarrow R^3$. A subset of transformations, known as "affine transformations", represents the set of all linear mappings of $R^3 \rightarrow R^3$ such that the resulting transformation is a rotation, scaling and/or shearing of an object and an optional translation. An affine transform is represented as a 4×4 matrix such that the fourth column represents a translation. Affine transformations matrices can be multiplied together to produce a chain of transformations.

As used herein, the term "quaternion" refers to a four-dimensional mathematical entity that represents the space of all rotations in $R^3$. For example, a single normalized quaternion (having a magnitude of 1) represents a rotation transform through some angle and axis about the origin of the current coordinate system. Multiplication of n>1 quaternions represents a series of rotations about the origin of the current coordinate system. Quaternions can be converted into the rotational component of an affine transformation matrix and mixed with other affine transformations.

As used herein, the term "rendering" refers to the process of constructing an image from image data, such as three-dimensional data. The rendering process can occur completely in hardware, completely in software or a combination of both hardware and software.

As used herein, the term "virtual camera" refers to a position in three-dimensional space from which a synthetic viewpoint is generated. A virtual camera may be employed to specify how three-dimensional anatomical image information should by displayed to a user upon rendering.

Embodiments of the present disclosure provide systems and methods for the rendering and displaying of a three-dimensional (3D) anatomical object on a display of a mobile computing device, where an image of the 3D anatomical object is rendered in a dynamic manner that is dependent on the orientation of the mobile computing device. The orientation of the mobile computing device may be employed to vary the perceived view of the 3D anatomical object. By changing the orientation of the mobile computing device, the orientation of the displayed 3D anatomical object moves responsively, such that, from the perspective of the user, the 3D anatomical object appears to be floating in front of them. In selected embodiments described further below, the user is able to manipulate the spatial orientation of the displayed 3D anatomical object through additional input to the mobile computing device.

Embodiments of the present disclosure therefore employ mobile devices with sensors for determining an orientation of the device, which can enable a more intuitive interaction of the user with anatomical and/or patient data. A mobile device configured according to embodiments presented below may act as a standalone simulation device, optionally providing a planning system, or act as an extension to augment traditional simulation and/or planning methods. As mobile computing devices become ubiquitous, further benefits exist for practitioners of medicine to plan surgeries or review plans on-the-go without having to be physically situated at a desktop workstation.

FIG. 1 illustrates a representation of 3D anatomical object data according to one embodiment of the disclosure. Three-dimensional anatomical object data may be represented and stored using a mesh representation 1, which is a collection of vertices 3 connected together by edges 4 to form polygons 2. For example, a 3D anatomical object may be represented as either a collection of meshes or a single mesh. Alternatively, the 3D anatomical object can be represented directly as volumetric data such that for each spatial coordinate there is an associated scalar value. This value represents the sensor measurement from the original scan data at that particular point in space. This volumetric element, or voxel representation, can be displayed via maximum intensity projections, or as 2D slices in the data volume.

Figure 2:
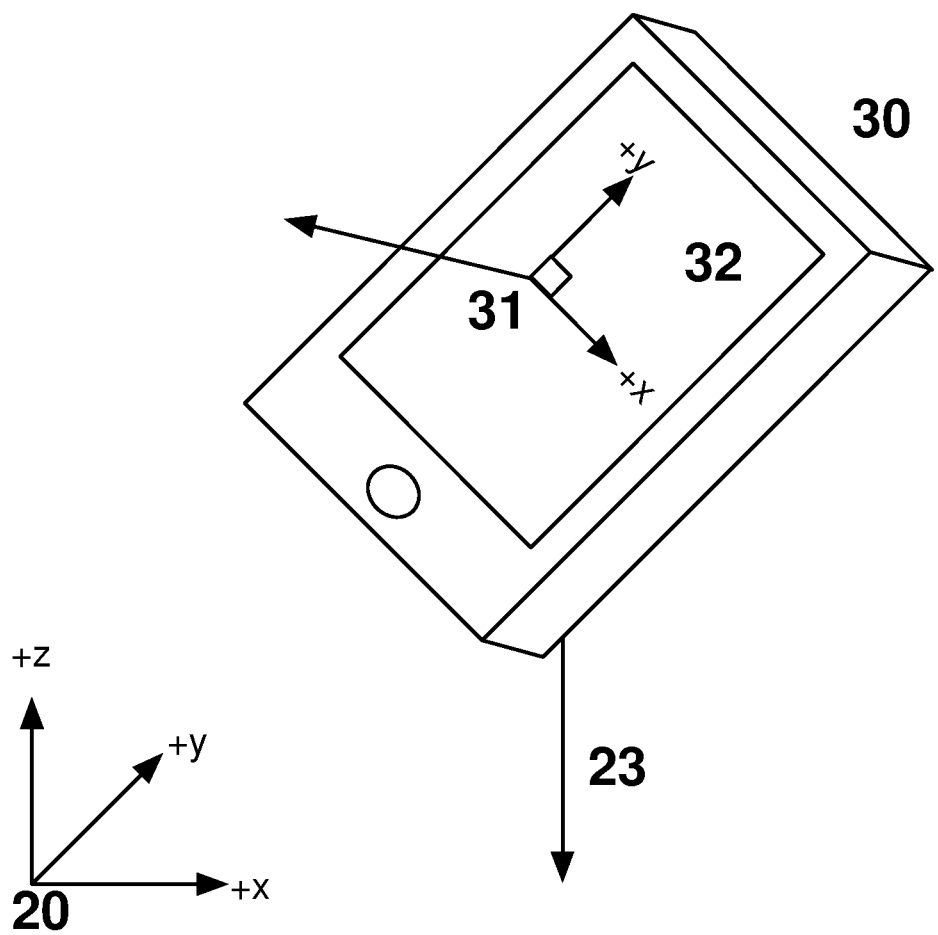
FIG. 2 is an illustration of the relationship between the local coordinate-system of the mobile computing device with respect to a global coordinate system, along with the direction of gravity with respect to the aforementioned coordinate systems.

FIG. 2 illustrates the different coordinate systems involved in the rendering of 3D anatomical image data. Mobile computing device 30 resides in global reference frame (x,y,z) 20. Mobile computing device 30 displays an image of 3D anatomical object 1 on a display 32. Device reference frame (x',y',z') 31 is shown as locally attached to mobile computing device 30. Device reference frame 31 varies relative to global reference frame 20 as the orientation of mobile computing device 30 is changed by a user. For example, device reference frame 31 may be translated and/or rotated relative to global reference frame 20 when mobile computing device 30 is translated and/or when an orientation of mobile computing device 30 is varied, respectively.

Virtual camera 22 represents the viewpoint of a user operating mobile computing device 30. While 3D anatomical object resides on display 32 of mobile computing device 31, virtual camera 22 is virtually located at a position external to that of mobile computing device 31, and the position and orientation of virtual camera 22 in global reference frame 20 do not change when the orientation of mobile computing device 31 is changed. Virtual camera 22 is thus effectively located on the surface of display 32, such that the distance between virtual camera 22 and object 1 determines how far "within" the display a user perceives object 1.

The final view presented to the user is created by issuing specific commands to the graphics application programming interface (API) provided by the operating system running on the mobile device 31. When given the relative position of the camera 22 to the object 1, affine transformations are determined that will present the user with the aforementioned view. The rendering is generated by a graphics API based on the parameters determined to place the camera 22 and object 1 in their appropriate positions.

The mobile computing device 30 resides in the same global reference frame, denoted by coordinate system 20, while an orientation of mobile computing device 30 is specified by device reference frame 31. The orientation of device reference frame 31 relative to that of global reference frame 20 may be determined by interrogating sensors that reside on or within mobile computing device 30. For example, output from such sensors may be employed to provide a determination of the orientation of device reference frame 31 relative to gravity vector 23.

Figure 3:
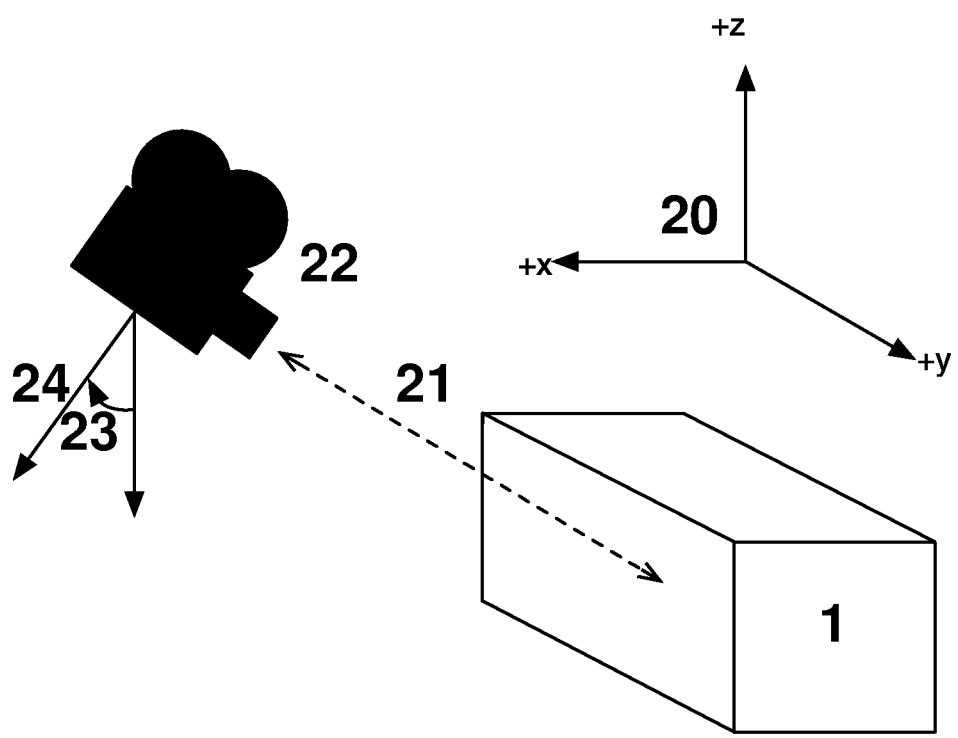
FIG. 3 is an illustration of the spatial relationships between the virtual, or synthetic, camera and the object being rendered or displayed.

As shown in FIG. 3, the virtual camera 22 is defined by its distance 21 from object 1 and by a "down vector" 24 perpendicular to the camera's line of sight and located in the same plane as that of the gravity vector 23. The model is rotated and positioned by finding a transform that maps mobile computing device-local coordinate system 31 to the global coordinate system 20. In one embodiment this is accomplished by transforming the gravity vector 23, such that its direction matches that of the virtual camera down vector 24. This is done for two reasons. First, relative to the device, the direction of gravity is not constant to that of the device, and therefore, its global coordinate frame. Second, the convention used in computer graphics is that the camera location is fixed at the origin of the coordinate system and the world is positioned relative to the camera.

Figure 4:
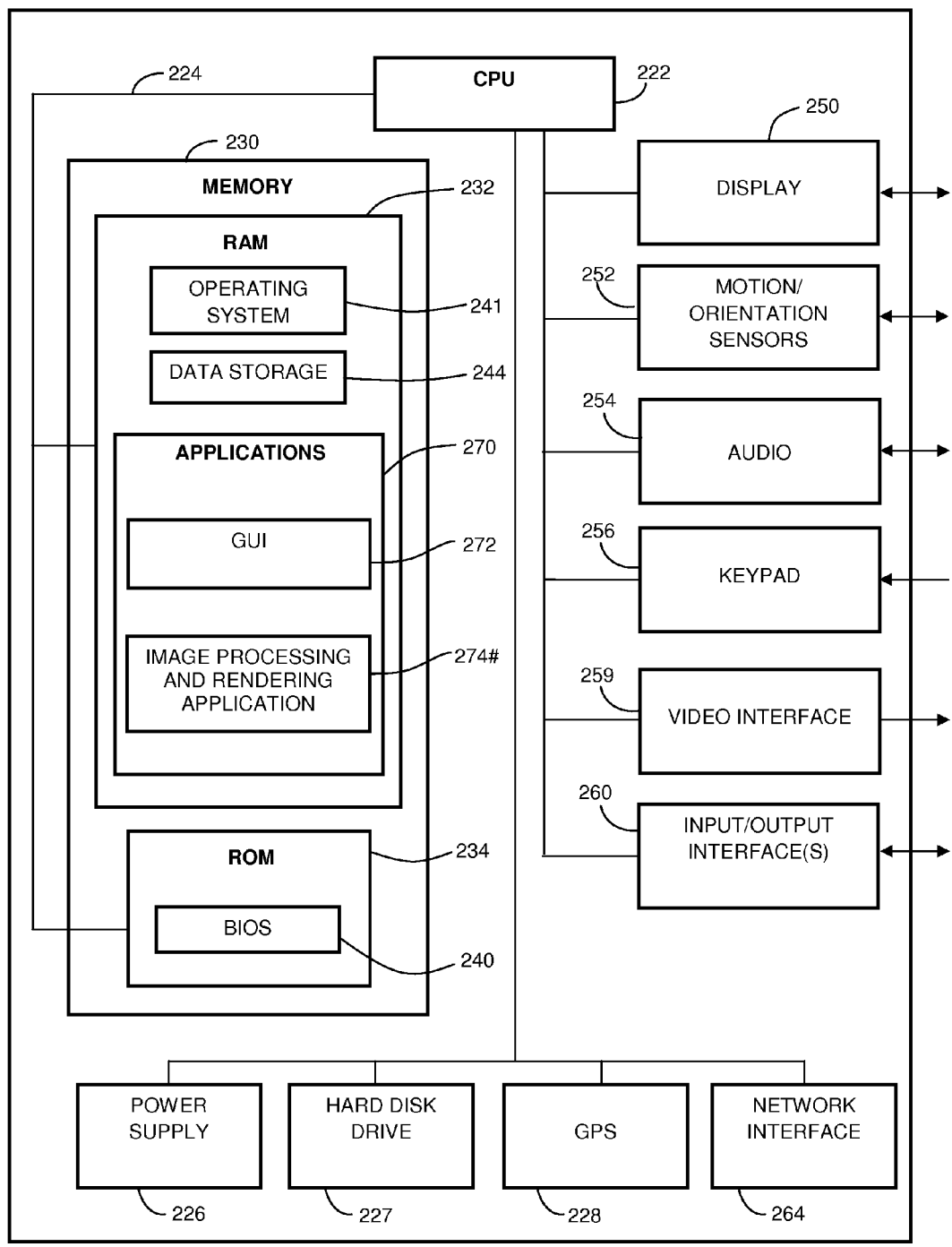
FIG. 4 provides an overview of a mobile computer device for performing embodiments of the disclosure.

FIG. 4 illustrates an example embodiment of a mobile computing device 30. Mobile computing device 30 may include many more or less components than those shown in FIG. 4. However, the components shown are sufficient to disclose an illustrative embodiment for practicing the present disclosure.

As shown in FIG. 4, mobile computing device 30 includes a processing unit (CPU) 222 in communication with a mass memory 230 via a bus 224. Mobile computing device 30 also includes a power supply 226, a display 250, and sensors 252. Mobile computing device may also include an audio device/interface 254, video interface 259, a keypad 256, an input/output interface 260, a global positioning systems (GPS) receiver 228, a hard disk drive 227 or other internal storage device, an a network interface 264.

Display 250 may be a liquid crystal display (LCD), gas plasma, light emitting diode (LED), or any other type of display used with a computing device. Display 254 may also include a touch sensitive screen arranged to receive input from an object such as a stylus or a digit from a human hand.

Sensors 252 may include a sufficient number and/or type of sensors to determine the direction of the gravity vector relative to mobile computing device 30. The sensors may include any one or more of a gyroscope, accelerometer, and/or digital compass, and a combination thereof.

The sensors may also provide sufficient information to determine the orientation of the mobile computing device 30 relative to the gravity vector, including a relative angle about a yaw axis. For example, the sensors may provide only the direction of gravity as a vector, or as gravity and relative rotation as a quaternion. In the latter case, the yaw information is already included in the quaternion, and an application running on the mobile device does not have to generate a quaternion from the gravity vector.

In one example implementation, the orientation of the device is derived from an onboard 3-axis accelerometer. To the device, gravity appears as a constant acceleration in a given direction as viewed from the device's coordinate system 31.

In one example embodiment, a three-axis accelerometer is employed to provide information associated with the orientation of the mobile computing device. In such an embodiment, the acceleration due to gravity may be separated from other sources of acceleration, i.e. movement. For example, a low-pass filter may be employed to separate the acceleration of the device due motion from the force applied due to gravity. For example, to produce suitably smooth motion so that small tremors in the user's hands are not noticeable, the cutoff frequency of the filter can be close to DC (a suitable example filter cutoff is about 5-10 Hz).

Such low-pass filtering can introduce a noticeable lag between when the device is moved and when the anatomical object moves. If the device has another sensor, such as a gyroscope, the method may include utilizing the information from that sensor to stabilize the accelerometer data without the need for a low-pass filter. This substantially eliminates the lag and makes the motion of the anatomical object more responsive to user input.

In one example implementation, the sensors include a three-axis gyroscope for determining the orientation and integrated motion (yielding position) of the computing device relative to that of the global reference frame. This can create the effect that an anatomical object's position is kept static in the global reference frame. When the computing device is moved away from the anatomical object, the object's size shrinks accordingly.

In another embodiment, sensors 252 may provide output signals for determining both relative motion and relative orientation of mobile computing device 30. In one example implementation, a three-axis accelerometer may be employed to detect relative motion for moving the displayed image of the anatomical object accordingly.

Power supply 226 provides power to mobile computing device 30. A rechargeable or non-rechargeable battery may be used to provide power. The power may also be provided by an external power source, such as an AC adapter or a powered docking cradle that supplements and/or recharges a battery.

Mobile computing device 30 may optionally communicate with a base station (not shown), or directly with another computing device. Network interface 264 includes circuitry for coupling mobile computing device 30 to one or more networks, and is constructed for use with one or more communication protocols and technologies including, but not limited to, global system for mobile communication (GSM), code division multiple access (CDMA), time division multiple access (TDMA), user datagram protocol (UDP), transmission control protocol/Internet protocol (TCP/IP), SMS, general packet radio service (GPRS), WAP, ultra wide band (UWB), IEEE 802.16 Worldwide Interoperability for Microwave Access (WiMax), SIP/RTP, Bluetooth™, infrared, Wi-Fi, Zigbee, or any of a variety of other wireless communication protocols. Network interface 250 is sometimes known as a transceiver, transceiving device, or network interface card (NIC).

Audio interface 254 is arranged to produce and receive audio signals. For example, audio interface 254 may be coupled to a speaker and microphone (not shown) to enable telecommunication with others and/or generate an audio acknowledgement for some action.

Video interface 259 is arranged to capture video images, such as a still photo, a video segment, an infrared video, or the like. For example, video interface 259 may be coupled to a digital video camera, a web-camera, or the like. Video interface 259 may comprise a lens, an image sensor, and other electronics. Image sensors may include a complementary metal-oxide-semiconductor (CMOS) integrated circuit, charge-coupled device (CCD), or any other integrated circuit for sensing light.

Keypad 256 may comprise any input device arranged to receive input from a user. For example, keypad 256 may include a push button numeric dial, or a keyboard. Keypad 256 may also include command buttons that are associated with selecting and sending images.

Mobile computing device 30 also includes input/output interface 260 for communicating with external devices, such as a headset, or other input or output devices not shown in FIG. 4. Input/output interface 260 can utilize one or more communication technologies, such as USB, infrared, Bluetooth™, Wi-Fi, Zigbee, or the like. Haptic interface 262 is arranged to provide tactile feedback to a user of the mobile computing device.

Optional GPS transceiver 228 can determine the physical coordinates of mobile computing device 30 on the surface of the Earth, which typically outputs a location as latitude and longitude values. GPS transceiver 228 can also employ other geo-positioning mechanisms, including, but not limited to, triangulation, assisted OPS (AGPS), E-OTD, CI, SAI, ETA, BSS or the like, to further determine the physical location of mobile computing device 30 on the surface of the Earth. It is understood that under different conditions, GPS transceiver 264 can determine a physical location within millimeters for mobile computing device 30; and in other cases, the determined physical location may be less precise, such as within a meter or significantly greater distances. In one embodiment, however, a mobile computing device may through other components, provide other information that may be employed to determine a physical location of the device, including for example, a MAC address, IP address, or the like. In another embodiment, GPS transceiver 228 may be employed to determine the relative translation of the device reference frame 31 relative to global reference frame 20.

In one embodiment, GPS transceiver 228 may operate with one or more other components of mobile computing device 30 to connect to a network to provide location information to another computing device. It should be noted, that where the user's configuration includes a GPS or other location detection device that is separate from mobile computing device 30, then that device may also include, in one embodiment, an ability to connect to a network to provide location information to another computing device.

Mass memory 230 includes a RAM 232, a ROM 234, and other storage means. Mass memory 230 illustrates another example of computer storage media for storage of information such as computer readable instructions, data structures, program modules or other data. Mass memory 230 stores a basic input/output system ("BIOS") 240 for controlling low-level operation of mobile computing device 30. The mass memory also stores an operating system 241 for controlling the operation of mobile computing device 30. It will be appreciated that this component may include a general purpose operating system such as a version of UNIX, or LINUX™, or a specialized client communication operating system such as iOS™, Android™, Windows Mobile™, or the Symbian® operating system. The operating system may include, or interface with a Java virtual machine module that enables control of hardware components and/or operating system operations via Java application programs.

Memory 230 further includes one or more data storage 244, which can be utilized by mobile computing device 30 to store, among other things, applications 242 and/or other data. For example, data storage 244 may also be employed to store information that describes various capabilities of mobile computing device 30. The information may then be provided to another device based on any of a variety of events, including being sent as part of a header during a communication, sent upon request, or the like. Moreover, data storage 244 may also be employed to store personal information including but not limited to address lists, contact lists, personal preferences, or the like.

In one embodiment, data storage 244 may be configured to store information associated with the rendering of 3D anatomical images. For example, data storage 244 may store 3D anatomical object data, which may be stored in mesh form (as described above). As described below, data storage 244 may also store computer-readable instructions for carrying out the methods described herein. At least a portion of the information may also be stored on a disk drive or other storage medium within mobile computing device 30, such as hard disk drive 227 or an external storage device, or the like. In one embodiment, a portion of the information may also be located remote to mobile computing device 30.

Applications 270 may include computer executable instructions which, when executed by mobile computing device 30, perform the methods described herein for the dynamic rendering of 3D anatomical images. In one embodiment, applications 270 may include graphical user interface 272 for facilitating user interaction, and image processing and rendering application 274 for processing 3D anatomical object data and sensor data and rendering the 3D anatomical object on display 250. The steps performed to process the sensor data and render the 3D anatomical object image data is described in detail below.

Embodiments of the disclosure can be implemented via the microprocessor(s) and/or the memory. For example, the functionalities described above can be partially implemented via hardware logic in the microprocessor(s) and partially using the instructions stored in the memory. Some embodiments are implemented using the microprocessor(s) without additional instructions stored in the memory. Some embodiments are implemented using the instructions stored in the memory for execution by one or more general purpose microprocessor(s). Thus, the disclosure is not limited to a specific configuration of hardware and/or software.

While some embodiments can be implemented in fully functioning computers and computer systems, various embodiments are capable of being distributed as a computing product in a variety of forms and are capable of being applied regardless of the particular type of machine or computer readable media used to actually effect the distribution.

At least some aspects disclosed can be embodied, at least in part, in software. That is, the techniques may be carried out in a computer system or other data processing system in response to its processor, such as a microprocessor, executing sequences of instructions contained in a memory, such as ROM, volatile RAM, non-volatile memory, cache or a remote storage device.

A computer readable storage medium can be used to store software and data which when executed by a data processing system causes the system to perform various methods. The executable software and data may be stored in various places including for example ROM, volatile RAM, nonvolatile memory and/or cache. Portions of this software and/or data may be stored in any one of these storage devices.

Figure 5:
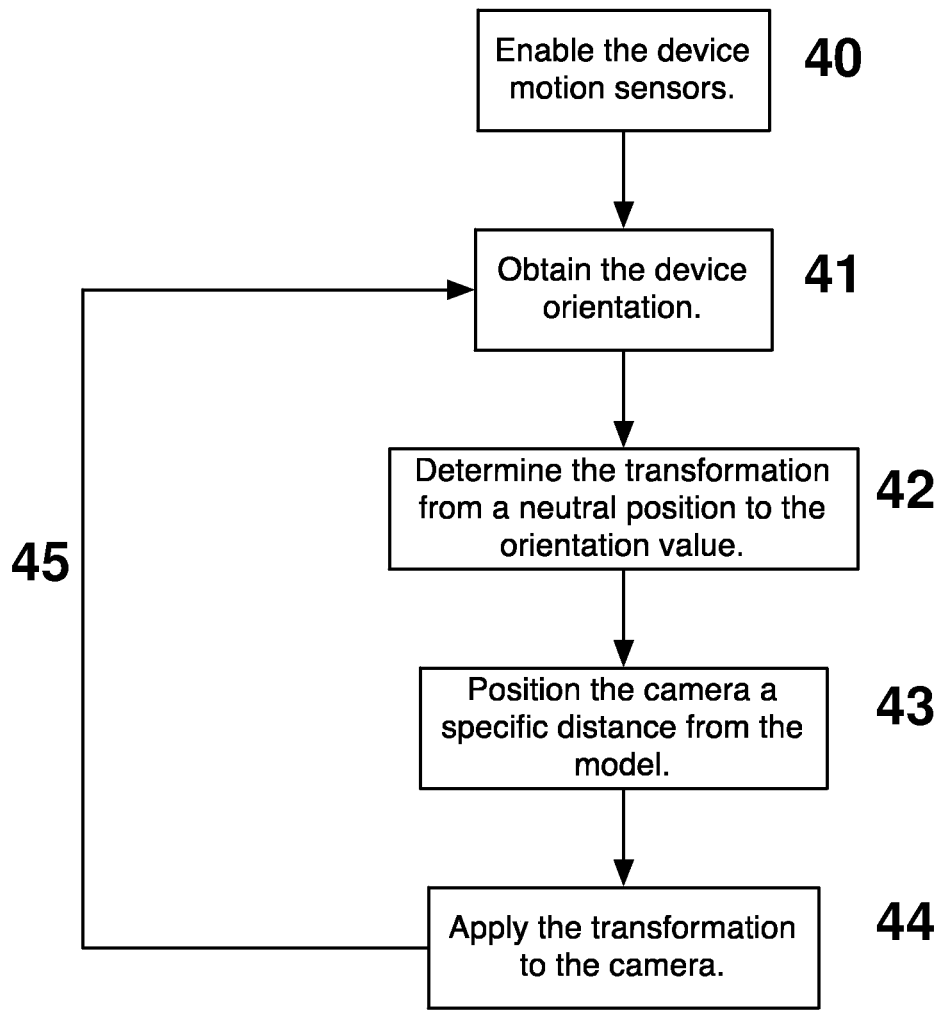
FIG. 5 is a flowchart demonstrating how the mobile computing device orientation is used to manipulate the rendered object.

As noted above, mobile computing device 30 is programmed such that the rendering of the 3D anatomical object is dependent on the orientation of mobile computing device 30. The process of rotating the object according to one embodiment is demonstrated in the example flow chart shown in FIG. 5. Upon initialization, the appropriate mobile computing device motion/orientation sensors are enabled in step 40. Such sensors may include, but are not limited to, gyroscopes and accelerometers, as described above. The orientation of mobile computing device 30 is then determined in step 41, such that the relative orientation of device reference frame 31 and global reference frame 20 is determined at least in part. With this available information, the method then determines a transformation in step 42 that will orient the anatomical object 1 such that reference vector associated with the object is aligned with the measured gravity vector 23. In one example, the pre-defined vector associated with the object is selected such that the pre-defined vector is aligned with the gravity vector when the display is positioned in a horizontal orientation.

After rotation, a transformation is found in step 43 that will position the camera a fixed distance away from the anatomical object. Finally the two transformations 44 (an orientational transformation and a translational transformation) are applied to the model, either serially or as a net transformation. This process repeats 45 as long as the application receives data from the sensors.

Figure 6:
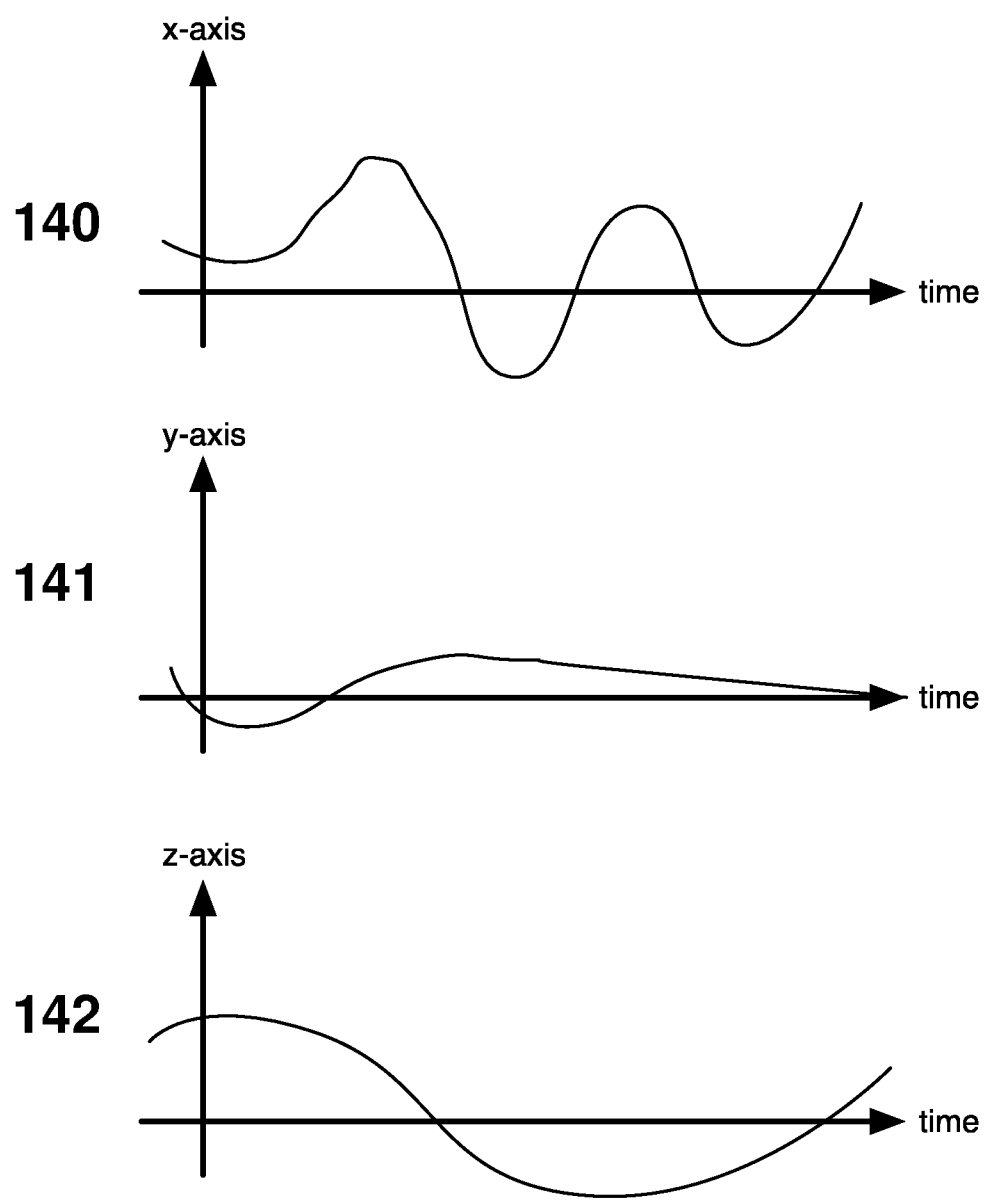
FIG. 6 is an example acquisition of gravity information through onboard accelerometer for each of the major axes as a function of time.
Figure 7:
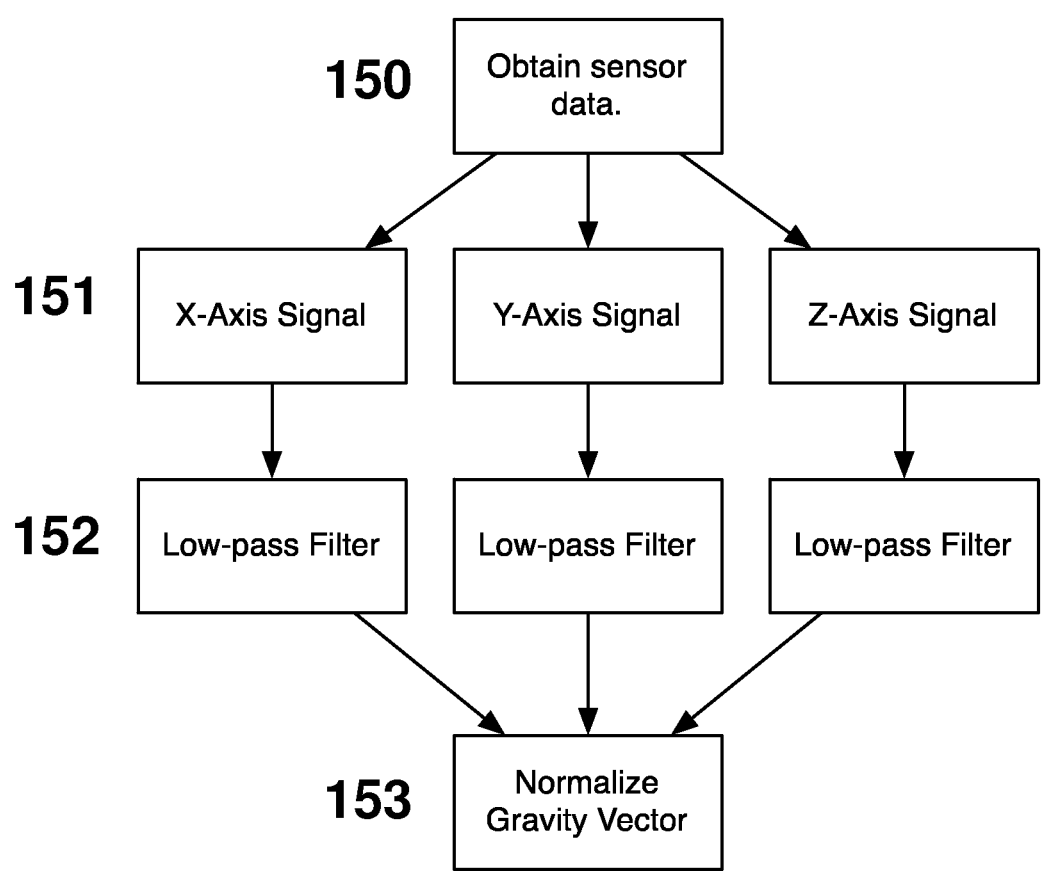
FIG. 7 is an example processing technique to filter and normalize gravity vector for object manipulation as expressed in the mobile device's own coordinate system.

In one example implementation, mobile computing device 30 determines the relative orientation of the device reference frame as follows. Sensor data is initially employed to determine the direction of the normalized gravity vector $\bar{g}=(g_y, g_y, g_z)$ in the device reference frame. In the simplest case, gravity information can be obtained through the onboard accelerometer. The observed acceleration, in the device coordinate system 20, is recorded for each of the major axes. As shown in FIG. 6 this can be interpreted as three time-varying signals along the x 140, y 141 and z 142 axes. The process for obtaining gravity, given this information, is outlined in FIG. 7. When a sample is generated 150, each axis 151 is filtered with a low-pass filter 152 such that only slow-varying signals are accepted. When combined into a vector, the new sample represents the gravity vector 24 as expressed in the mobile device's 30 own coordinate system 31. Since only the direction is necessary, the vector is normalized 153 to remove the effects on magnitude that the filtering may have had.

Figure 8:
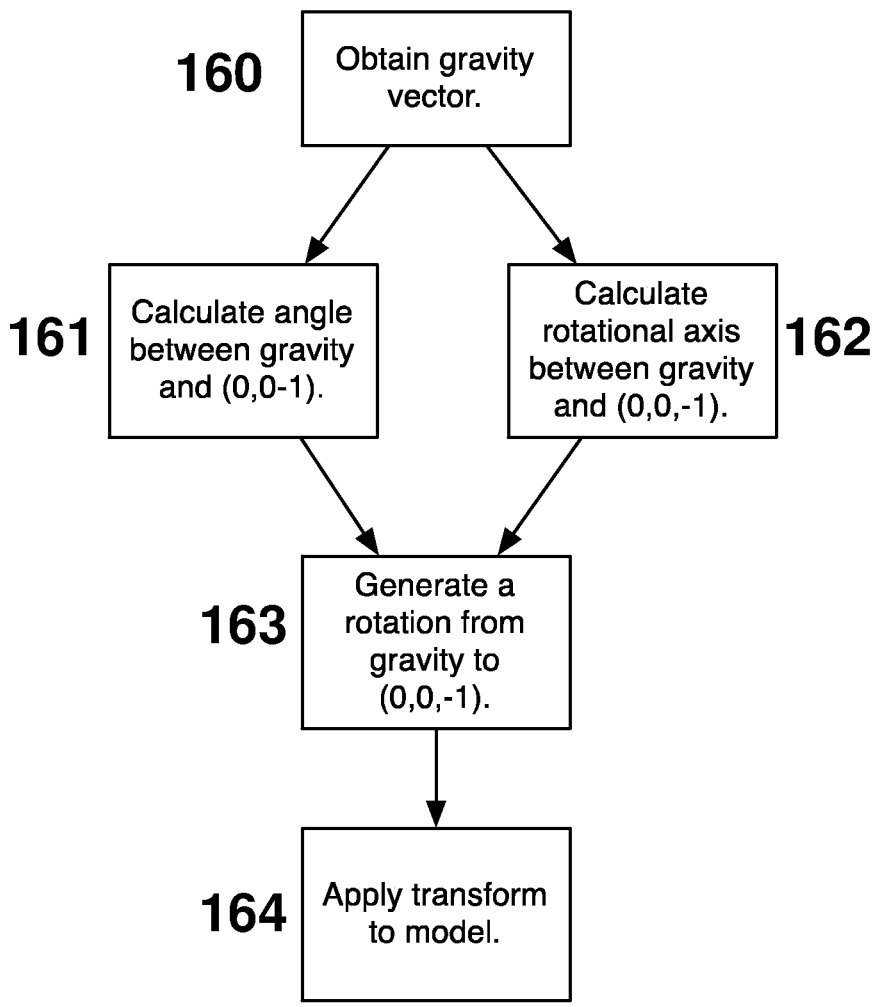
FIG. 8 demonstrates an example of how the gravity direction is used to obtain a suitable transformation, such that the virtual object can be rotated.

With the orientation of the gravity vector within the device reference frame known, an affine transformation R is determined in step 42, such that the application of the transformation R to the anatomical object will rotate the reference vector to align with the gravity vector. As noted above, the reference vector $\bar{r}$ is a reference vector associated with the orientation of the anatomical object within the coordinate frame of the mobile computing device, such that the reference vector is initially aligned with the gravity vector when the mobile computing device is positioned in a reference orientation. In one example, the reference vector is given in the coordinate frame of the mobile computing device as $\bar{r}=(0,0,-1)$, such that the reference orientation is a horizontal orientation. The affine transform R may be obtained by finding the quaternion q that represents the rotation of $\bar{g}$ to $\bar{r}$. FIG. 8 shows an example of how the gravity direction is used to obtain a transform. Given the direction of gravity 160, two items are necessary to generate the transformation: the angle between the two vectors 161 and the axis of rotation 162. From this data, a suitable transformation can be found 163 and used to rotation the anatomical object 164.

Figure 9:
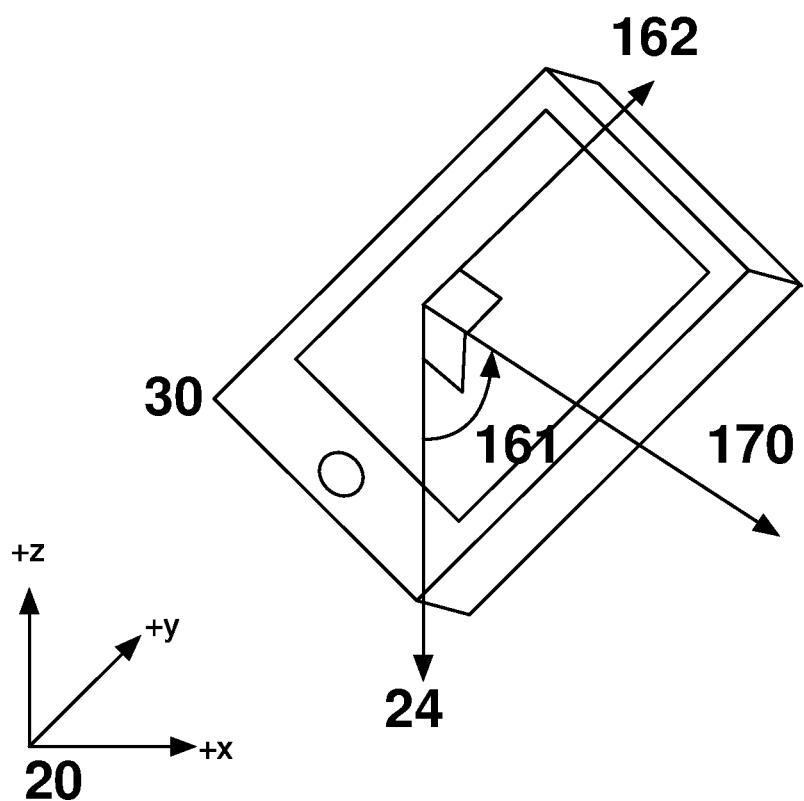
FIG. 9 demonstrates a process to calculate a suitable transform, or equivalently a quaternion to correctly orient the virtual object.

A specific example of the determination of suitable transform R, or equivalently, quaternion q, is shown in FIG. 9. In the figure, the device is shown oriented to the world coordinate system 20. In this case, the gravity vector 24 will always point in direction of the negative z-axis. The reference vector 170 is chosen, in this example, such that it will always point into the screen, regardless of the direction of the handedness of the coordinate system. In this example, the device coordinate system is assumed to be left-handed so that the z-axis comes out of the screen.

To correctly orient the anatomical model, the transform is chosen such that, if applied to the gravity vector, the gravity vector would be rotated onto the reference vector as the gravity vector is variable with respect to the device. To obtain this transform two items are necessary: the angle 161 between the gravity vector and the reference and the axis of rotation 162. In the following derivation, all vectors have been normalized so that their lengths are unity. The order in which the two items are calculated is not important. The angle θ is obtained by $$\theta = \arccos(\bar{g} \cdot \bar{r})$$

and the axis $\bar{a}$ is obtained by $$\bar{a} = \frac{\bar{g} \times \bar{r}}{\|\bar{g} \times \bar{r}\|}$$

Given the angle and axis, a quaternion q can be constructed. In one representation, a quaternion is a 4-tuple such that q=(x,y,z,w). In another representation, a quaternion is a combination of a vector and a scalar such that $q=\bar{v}+s$. The vector component of the rotation quaternion can be expressed as:

$$\bar{v} = \bar{a} \sin(\theta/2)$$

and the scalar component can be expressed as:

$$s = \cos(\theta/2)$$

To ensure that the quaternion is rotated, it is normalized so that its magnitude is equal to unity. The normalized quaternion can then be expressed as a rotation matrix R using:

$$R = \begin{bmatrix} 1-2(y^2+z^2) & xy-wz & xz+wy \\ xy+wz & 1-2(x^2+z^2) & yz-wx \\ xz-wy & yz+wx & 1-2(x^2+y^2) \end{bmatrix}$$

To demonstrate this method, consider the trivial case where reference vector and gravity vector are aligned such that $\bar{g}=\bar{r}=(0,0,-1)$. In this case, the dot, or inner product will be $\bar{g}\cdot\bar{r}=1$ and the corresponding angle between the two vectors is 0. Similarly, the cross product between the two identical vectors will be $\bar{g}\times\bar{r}=(0,0,0)$. The quaternion generated from this rotational axis and angle will be $\bar{q}=(0,0,0,1)$ when represented by a 4-tuple. As a rotational transformation matrix, the quaternion is represented as:

$$R = \begin{bmatrix} 1 & 0 & 0 \\ 0 & 1 & 0 \\ 0 & 0 & 1 \end{bmatrix}$$

This is because the two vectors were aligned the resulting transformation is identity. As the two vectors begin to diverge, the resulting transformation is a rotation that takes gravity to the reference vector.

To position the virtual camera 22, an affine transform T is determined in step 43 such that if the camera is located at the origin of the global reference frame with coordinates, $\bar{o}=(0,0,0)$ then the anatomical object 1 is located a distance, d, from the camera 21 such that its position is $\bar{p}=(0,0,d)$. The distance d is chosen based on a number of factors, such as a radius (radii) of the anatomical object(s) being viewed or how close the user wishes the camera to be to the object. The sign of d depends on the handedness of the coordinate system. If the positive z-axis is coming out of the screen, d must be negative, otherwise it must be positive.

In one embodiment, the distance d is prescribed automatically by the application and need not be provided by the user. For instance, if the anatomical model has a radius of r units, then a suitable value of d may be chosen such that the object is completely visible on the display surface 32. One method to accomplish this is to choose d so that $$d = \frac{r}{\tan(\theta/2)} + K,$$

where θ is the field of view and K is a fixed constant used to ensure the camera is a minimum distance from the object. Additionally or alternatively, the user may provide input to determine and/or scale the value of d, for example, using gestures such as "pinch-to-zoom". The "pinch-to-zoom" feature may be implemented to move the camera and changes the d value in real time.

Figure 10A:
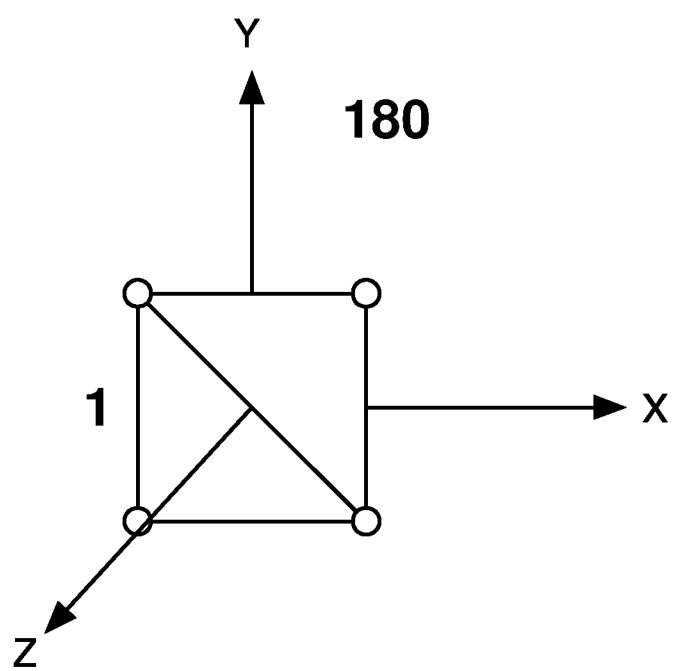
FIG. 10a provides an example of how an object can be transformed.
Figure 10B:
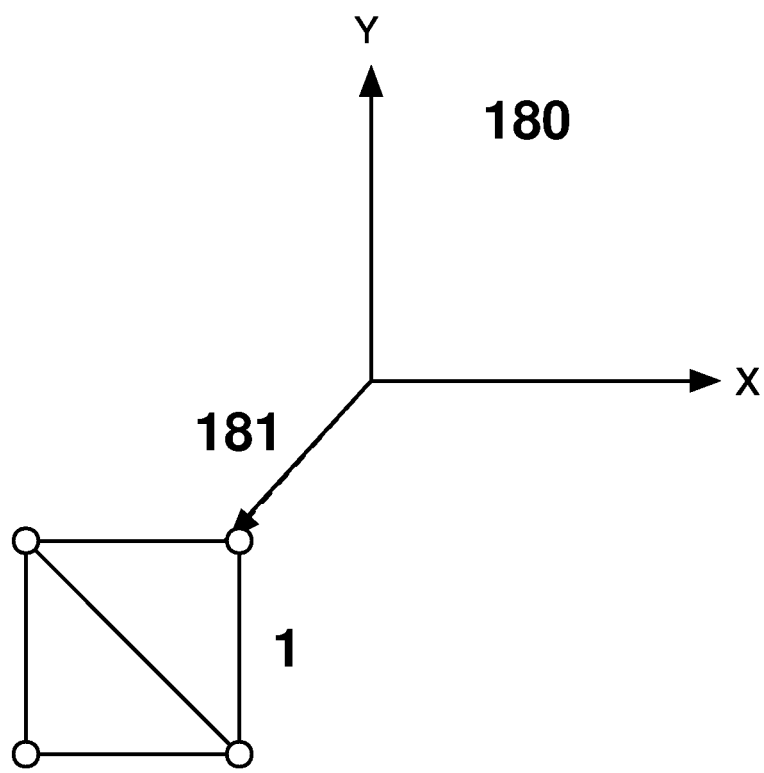
FIG. 10b provides an example of how the object can be translated.
Figure 10C:
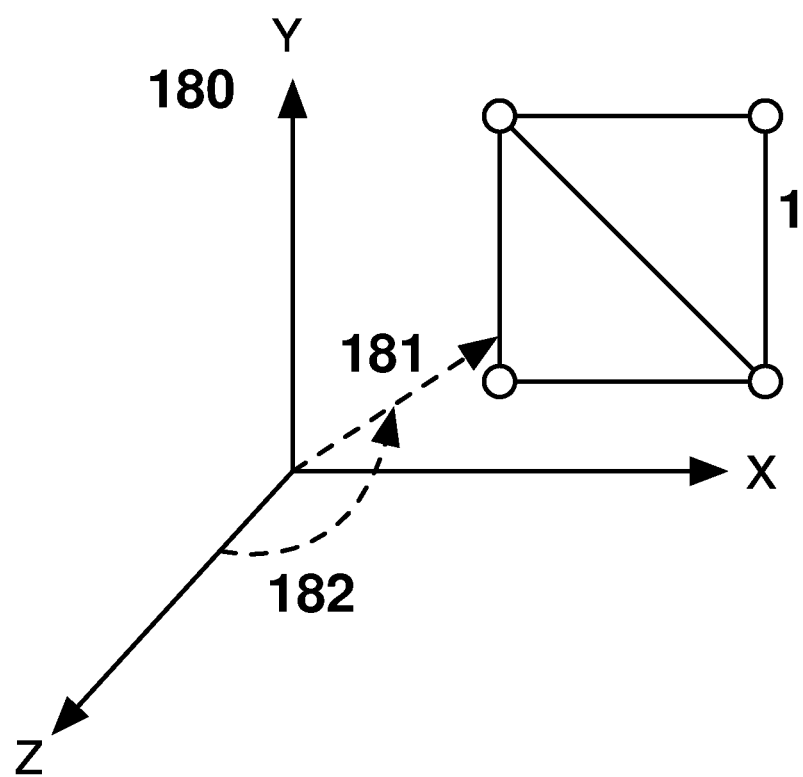
FIG. 10c provides an example of how the object can be rotated.

The two transforms are concatenated to produce a new transform H in step 23, such that H=RT. This transform is applied in step 44 to the anatomical object 1 to give the appearance that the anatomical object is stationary, while the user manipulates the mobile computing device 30. FIG. 10 provides an example of how an object 1 is transformed. In FIG. 10*a*, the object is located at the origin of the coordinate system 180. Should the object not be located at the origin, the average value, or centroid, of the object vertices is first subtracted to center the object prior to performing the procedure. This represents the default position and orientation of the object regardless of the current device orientation. In FIG. 10*b*, the object is translated 181 along the z-axis based on the value of d in step 43. In this example, d is a positive value and it is moved along the positive z-axis. In FIG. 10*c*, the object is rotated 182 based on the rotation transform R.

Figure 11:
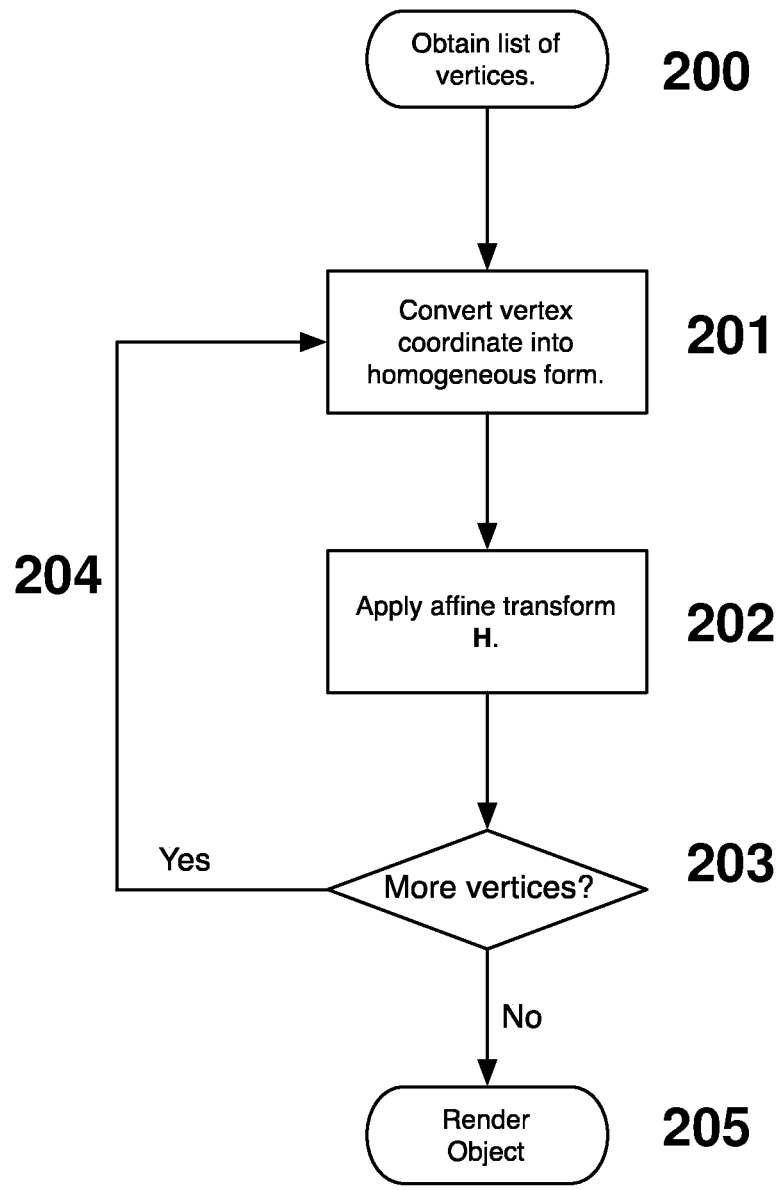
FIG. 11 provides an example of transforming a mesh through a serial process.

The transformation procedure may be applied to anatomical object either serially or in parallel. FIG. 11 provides an example of transforming a mesh through a serial process. Given a set of vertices 200, the three dimensional coordinate of a vertex is first converted into its homogenous equivalent 201 such that it's new coordinate is (x,y,z,1). An affine transform is applied to the vertex 202 to produce a transformed vertex position. If there are more vertices 203 then the process repeats 204 until all vertices in the object have been transformed. After the affine transformation has been applied to all vertices the object is rendered 205.

To transform the object using a parallel method, a 4×N matrix, where N is the number of vertices 3 in the object, is constructed such that each column in the matrix contains the homogeneous representation of each vertex:

$$V = \begin{bmatrix} x_1 & x_2 & & x_N \\ y_1 & y_2 & \cdots & y_N \\ z_1 & z_2 & & z_N \\ 1 & 1 & & 1 \end{bmatrix}$$

In this example, the final transformation matrix H is $$H = \begin{bmatrix} R & \bar{p} \\ 0 & 1 \end{bmatrix}$$

where R and $\bar{p}$ are the rotation matrix and offset vector, respectively. The object is transformed by simply performing V'=HV.

The preceding steps may be repeated to provide real-time updating of the rendered orientation of the anatomical object in response to the changing orientation of the mobile computing device. As shown in step 45, each time the anatomical object image is rendered, the motion and orientation sensors are sampled and the process of obtaining the transform is performed.

In another embodiment, using the motion information obtained from the accelerometer and gyroscope, the size of the anatomical object can be changed. When the mobile computing device is first used, its current position in space is recorded. By moving the mobile computing device towards and way from the apparent location of the anatomical object, the recorded acceleration can be used to determine how much closer or father away the camera is from the object, thus updating the value of distance d. When combined with the orientation information it can be used to simulate a stationary object in the user's field of view, in effect fixing its position in space relative the user.

The process of transforming the rendering of the anatomical image via the present method enables a user to interact with the virtual anatomical image in a dynamic manner, where the anatomical object appears stationary and the user effectively rotates around the anatomical object. The user is thus given a sense that the anatomical object is floating in a space behind the screen of the mobile computing device and that they are observing it through a "window".

Prior to rendering, a user may be presented, through the user interface, with a number of different, preprocessed anatomical objects or models for selection. Anatomical object imaging data may be stored within memory of mobile computing device 30, or obtained from an external source, such as through a network connection. For example, the mobile computing device may communicate with or access a remote server and securely transmit anatomical object image data onto the medical mobile computing device. Once an anatomical object has been selected and rendered on the display according to the above steps, the user can manipulate the display of the anatomical object in a number of ways. The anatomical object data may be provided based on measurements of a real anatomical object, or may be artificial or simulated data.

In one embodiment, three-dimensional data obtained from performing an imaging modality is first converted into a format that can be read and/or processed by mobile computing device 30, such as a digital imaging and communications in medicine (DICOM) image. The data may originate from a number of imaging modalities such as, but not limited to, magnetic resonance imaging (MRI), fluoroscopy, computed tomography (CT), positron emission tomography (PET), ultrasound (US), optical coherence tomography (OCT) and single photon emission computed tomography (SPECT) scans. The data may also be segmented into smaller models or retained as a single, large model. After the conversion, the data is transmitted and stored on the mobile computing device, or storage media, for future use.

It is to be understood that the embodiments disclosed herein are not limited to merely viewing rendered anatomical object image data, but may also be employed for interacting with it the anatomical object virtually for surgical training and/or planning. To this extent, different input modalities available to the mobile computing device may be utilized. Examples of the available inputs include touch sensitive regions (not just limited to the display), orientation and motion sensors, and cameras capable of capturing low, medium and high-resolution video. Any or all of these inputs may be utilized to manipulate the rendering of stored data according to various embodiments disclosed herein.

In one embodiment, the aforementioned methods may be employed for surgical training and/or preparation. As discussed in further detail below, the mobile computing device may also contain, or obtain from a remote server or storage location, a collection of three-dimensional models of surgical devices that may be available to the user at the time of surgery. The surgical devices may be surgical implants or fastening devices such as screws. After having processed and co-rendered the 3D surgical device object image data, the user may interact with both the anatomical object and the surgical device using the mobile computing device.

In one example, the surgical device may be a screw, and the mobile computing device may be employed for training and/or surgical planning. After screw placement is complete, the user may be able to view the screw placement in relation to both the original imaging data and the processed 3D model to allow for an assessment of the positioning based upon the user's training and experience.

For example, the aforementioned embodiments may be utilized for spinal surgery training or preparation. A generic, or anonymous, skeletal model may be stored on the mobile computing device for training purposes. A collection of standard screw sizes may also be stored on the mobile computing device. Pedicle screw volumes that could potentially injure or kill a patient, for example the placement of a pedicle screw that intersects the spinal, may also be stored within the model data.

The user interacts with generic model data and places the screw using standard surgical methods. This process can be repeated multiple times for as many screws that need to be inserted for the full implementation of the surgical construct. If the screw passes through a marked volume, such as the spinal canal, the user is alerted to the intrusion through audio, visual and haptic feedback. After placement is complete, the mobile computing device determines the accuracy of the placement by comparing the entry point and angle to a list of entry points and angles appropriate for the model. The user receives feedback on the overall accuracy and the number of surgical incidents, where a screw could have resulted in surgical complications.

Figure 12:
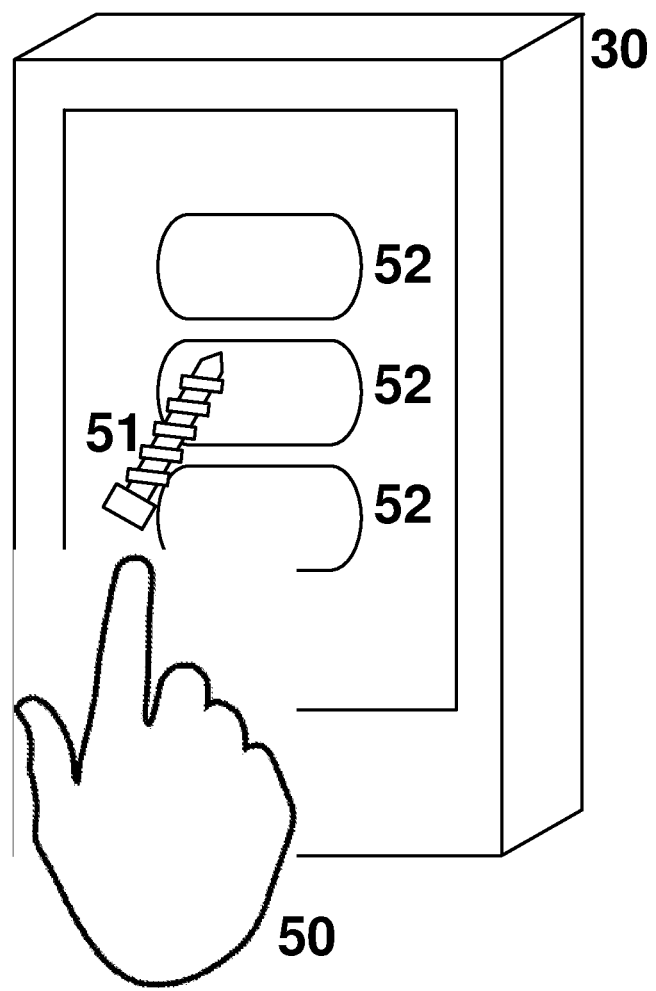
FIG. 12 is an example of touch-based user interaction with the mobile computing device.

FIG. 12 represents a basic method of facilitating user interaction with the mobile computing device for training and planning purposes. In one embodiment, the user 50 places a screw 51 onto a vertebral body 52 through touch-based manipulation. Given information about the camera 22, the screw 51 can be orientated with the camera so that the line of sight 21 is parallel to the insertion vector of the screw.

Figure 13:
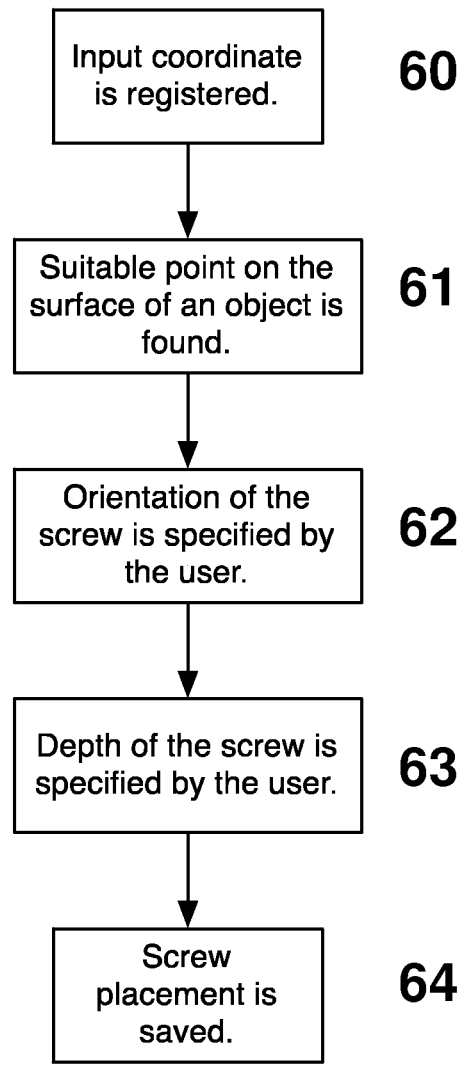
FIG. 13 is a flowchart of the method used to determine the entry location of a screw on the surface of an object.

An example method of the virtual placement of a screw is presented in FIG. 13. In step 60, an input coordinate, $\bar{x}$ is first registered that indicates the location of the input in the global coordinate system 20. This coordinate can be a result of an automatic process, such as being derived from the orientation of the device or from a direct input by the user. In one embodiment, given the orientation 24 of the camera 22 (which is determined as described above), a point, $\bar{p}$, on the surface of the object 1 is found in step 61 such that the point is a projection of $\bar{x}$ onto the surface of the object. With the entry point fixed, the entry angle of the screw is obtained 62. In one example, the screw orientation may be determined such that the direction of the screw is equal to the direction of the camera (the screw may also be displayed in such a way to make the entry point easier to observe (e.g. translucent)). In another example, the entry point and angle may be determined through touch-based interaction or through another form of user input. The depth of the screw is obtained 63 in a similar manner in that through either a touch or gestural input the user is able to specify how deep the screw will penetrate the particular anatomical object. The screw parameters are stored for later use in step 64.

Figure 14:
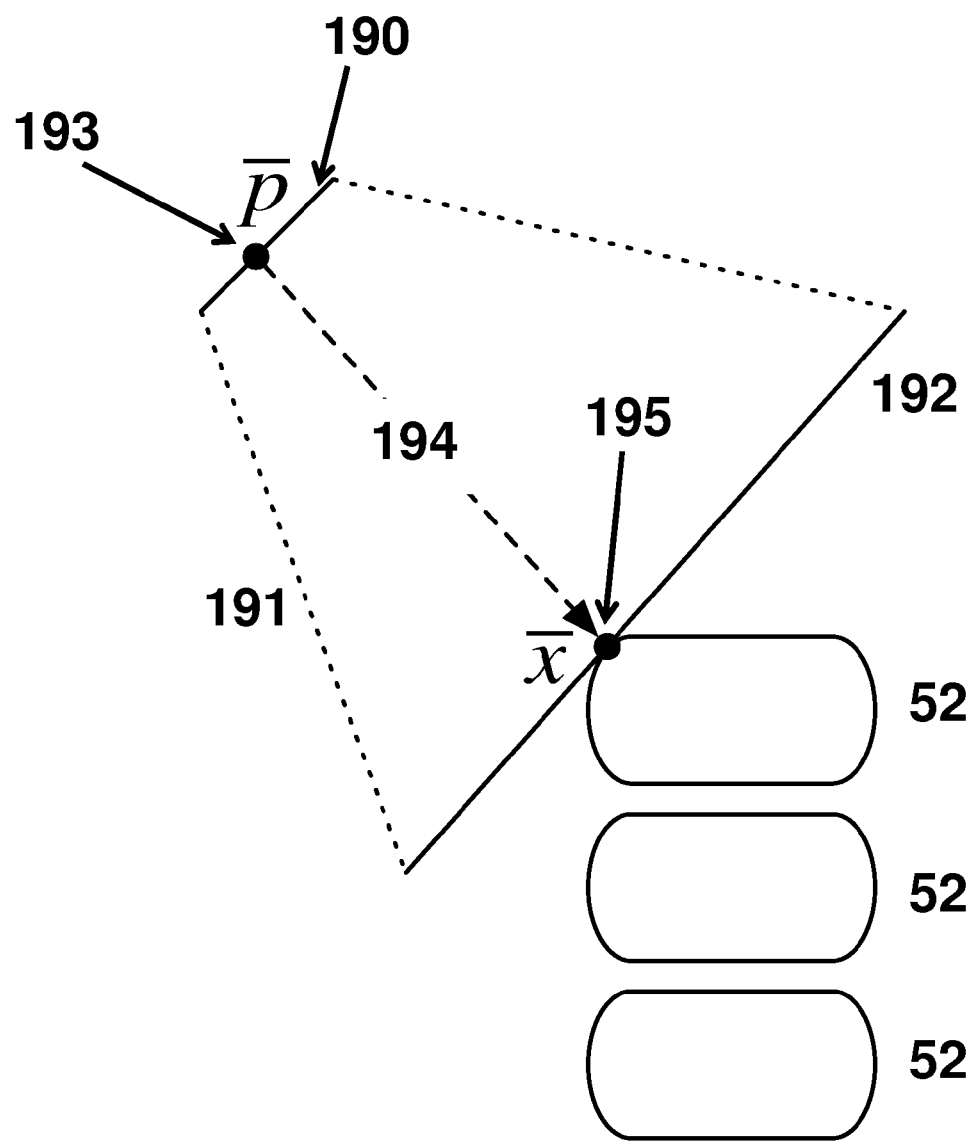
FIG. 14 shows the relationship of a point and how that point is projects onto an object.

FIG. 14 shows the relationship between $\bar{p}$ and $\bar{x}$. The screen of the device 190 can be interpreted as a plane located at the position of the camera. The location of the input $\bar{p}$ 193, is a point on the plane. As the camera has a known angular value for its field of view, this constructs a view frustum 191 that describes the volume that is visible to the user. The location of $\bar{x}$ 195 is the projection 194 of $\bar{p}$ onto a plane 192 that touches a particular anatomical object 52.

Figure 15:
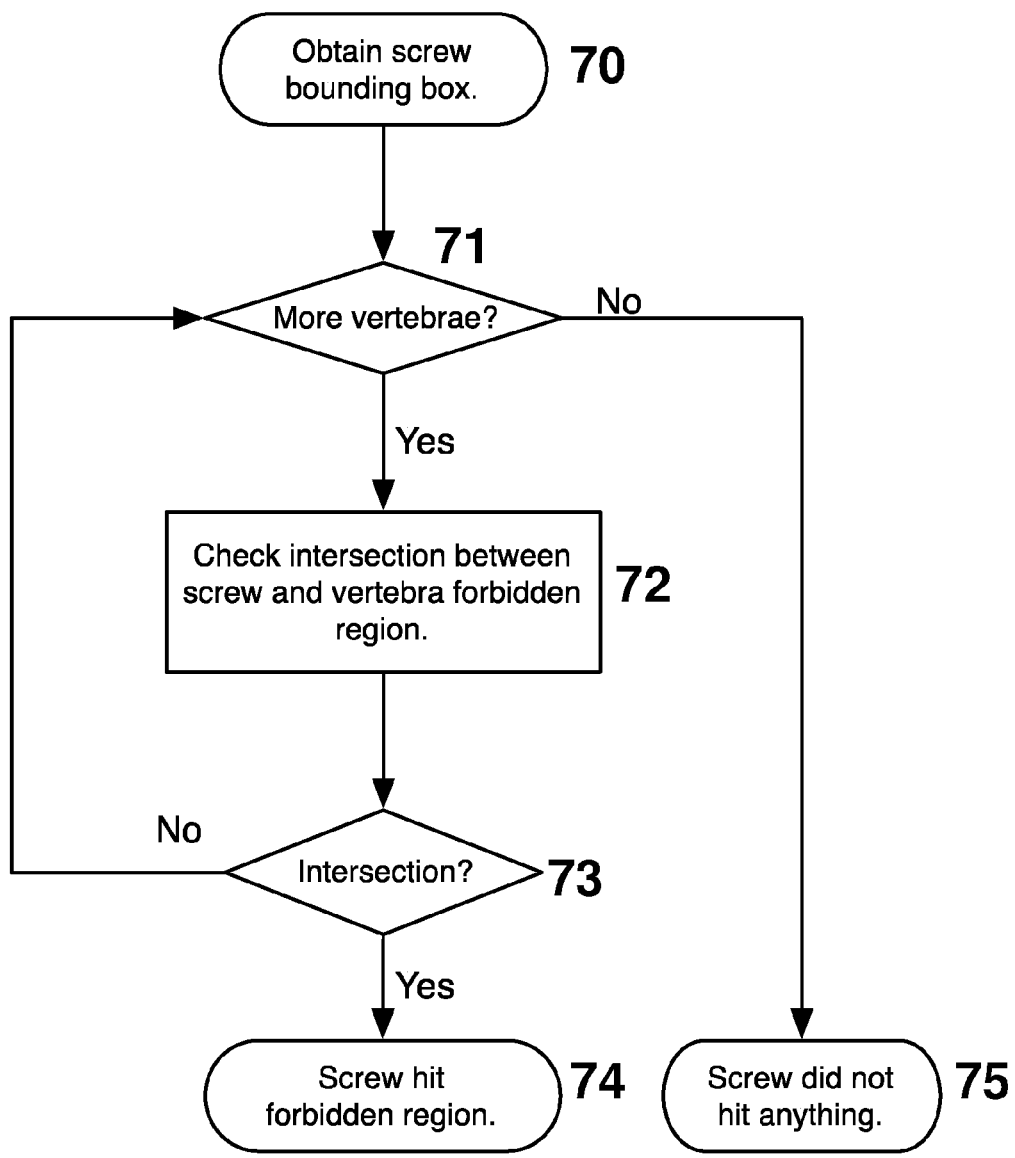
FIG. 15 is a flowchart of the algorithm used to determine whether or not a collision has occurred between the screw and a defined "injury volume".

When used for training, the mobile computing devices and methods disclosed herein can provide feedback to the user in a number of ways, such as, but not limited to, visual indicators, audible warnings or haptic feedback. In one embodiment, when used for training surgeons in surgical screw placement, the user must be taught in what regions the screw can, and cannot, be inserted. FIG. 15 presents a description of a method to ensure a screw will produce patient complications. Each vertebral body 52 is defined via boundary data that outlines forbidden regions, where if an interventional mobile computing device (e.g. pedicle screw) were to intersect this region, patient complications would occur. Given a convex hull, for example, but not limited to, a bounding box, around the screw 70, each mesh 71 comprising the complete object is compared to the hull surrounding the screw. An intersection test is performed between the screw and the mesh 72. Should an intersection 73 occur, a notification is presented that the screw is in a region that would harm the patient 74. Should no intersections be detected 75 it is assumed that the screw has been placed without inducing any patient complications.

As skeletal models could be processed to yield extra training data, information about proper screw placement could also be stored alongside these anatomical models. After placement is complete, the angle of entry 62 may be compared to a list of known angles for the particular model. The user's screw placement may be then graded based on how close their placement angle was to the optimal angle for the particular model.

Figure 16:
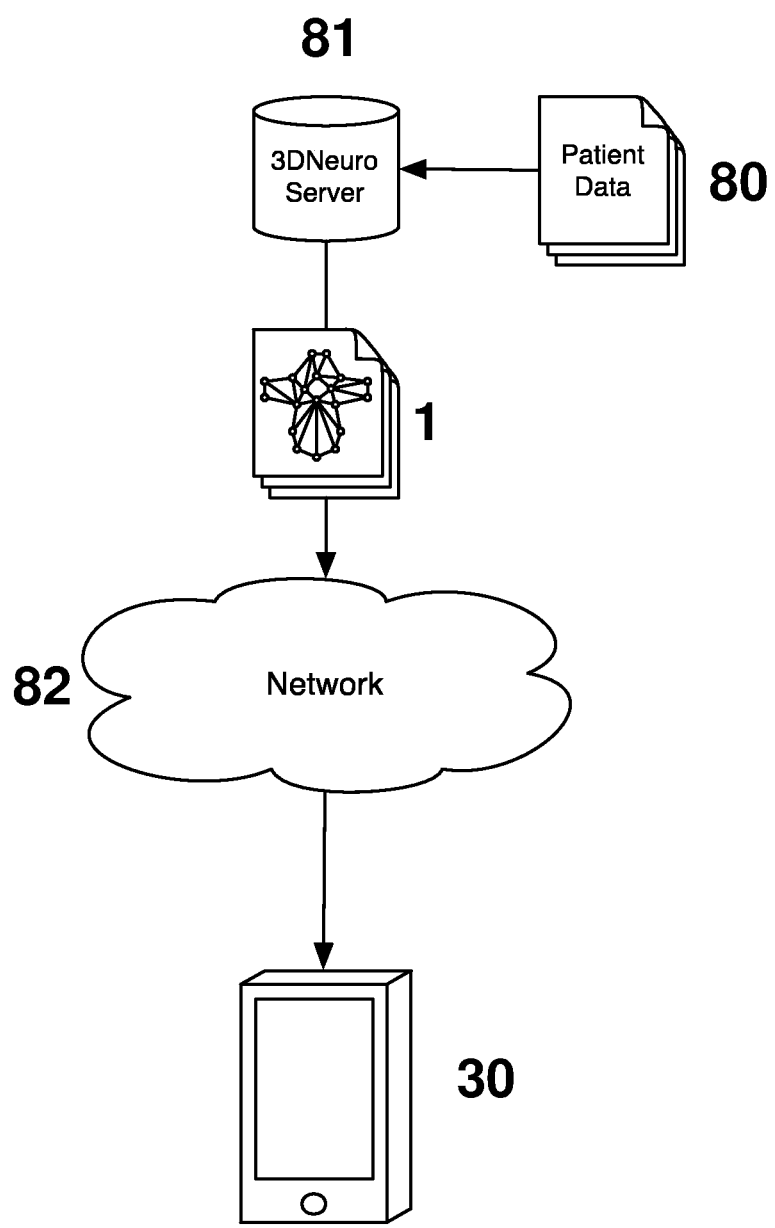
FIG. 16 is a schematic diagram of the method involving remote access of patient data.

FIG. 16 describes an example of how patient data could be stored and transmitted to the mobile computing device. Prior to use of the mobile computing device, the patient data 70, which may originate from a number of different sources, is stored on a remote server 71. The server converts the patient data 70 into a representation 1 that is readable by the mobile computing device. Upon conversion, the information is transmitted 72 to the mobile computing device 30 that is executing the method. In one embodiment, the server 71 is a computer to which the user has no direct access or knowledge thereof. In this embodiment the network 72 is a computer network such as, but not limited to, a Local Area Network (LAN), intranet, or the Internet. In another embodiment, the server 71 is an application running on a computer to which the user has secure access. In this embodiment, the user directly loads the mesh data 1 directly onto their mobile computing device 30.

Figure 17A:
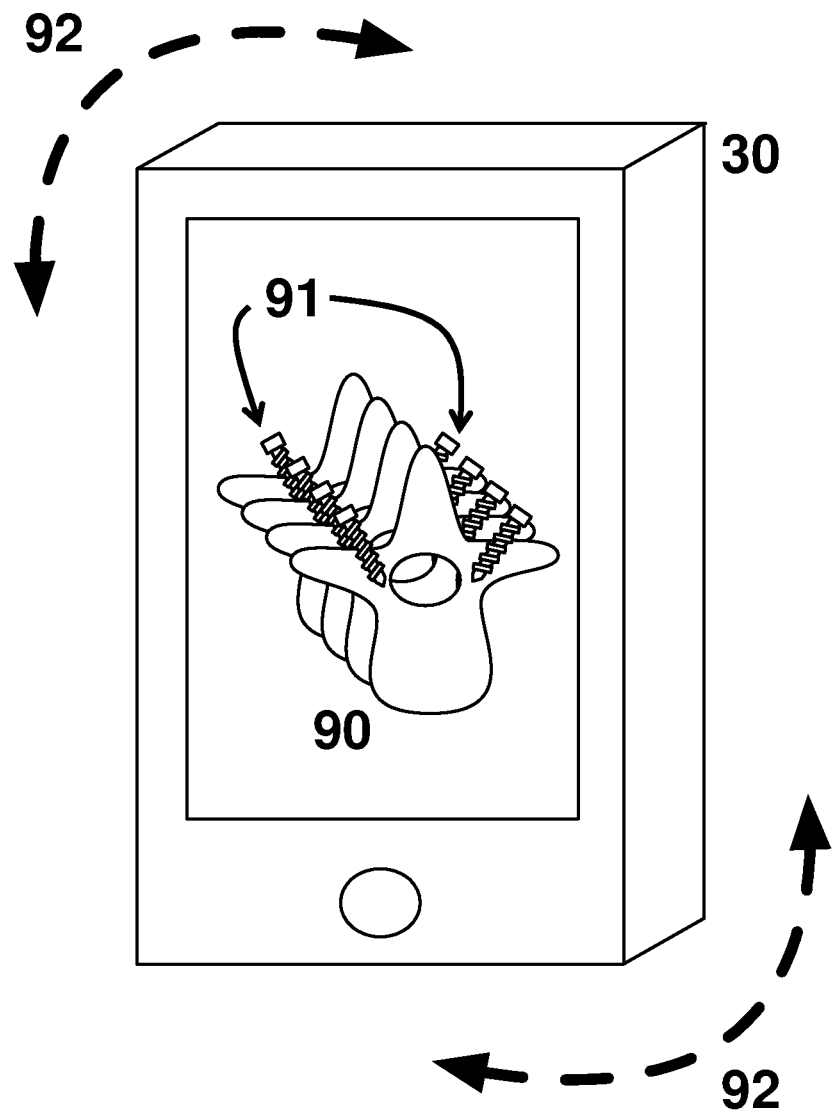
FIG. 17a is an example of screw placement review using the mobile computing device orientation sensors.
Figure 17B:
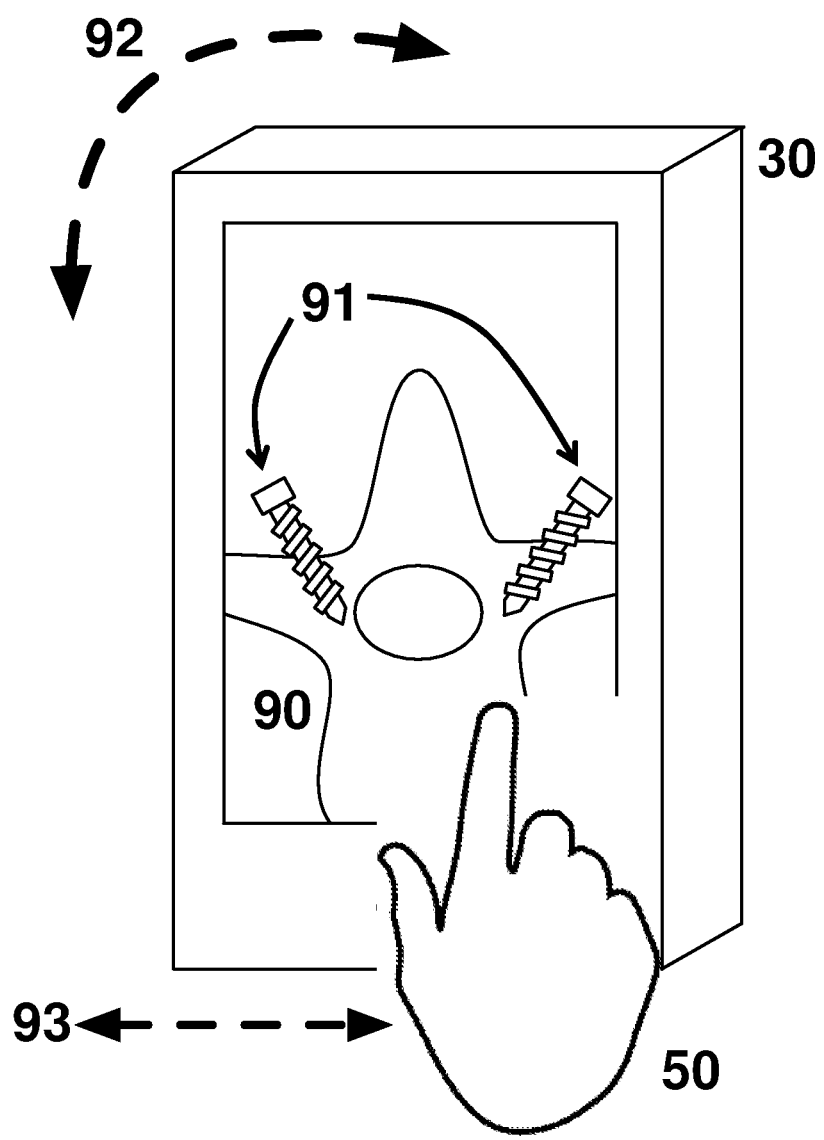
FIG. 17b is an example of screw placement review using a touch-based orthogonal view.

Screw placement is done in a similar manner to the one used for training. In FIG. 17a, the user manipulates 92 the mobile computing device 30 as before. The screws 91 are placed into the three-dimensional representation of the data 90 obtained from the patient. This is termed the "perspective view". In FIG. 17b, the representation of the data 90 is shown as a projection onto one of the major coordinate planes, for example, but not limited to, the x-y plane. The user 50 can manipulate this view through touch and gestures 93. This is termed the "orthographic view" and replicates the user looking at a conventional medical imaging representation. This treatment planning information (e.g. pedicle screw entry point, screw trajectory) could then be stored and transmitted for use during the actual surgery in combination with surgical navigation or robotic navigation technology.

When developing a surgical plan, a surgeon must be able to simulate what will be done during the planned surgical procedure with sufficient precision. To that end, the mobile computing device may utilize a front-facing camera to assist with planning. Through simple gestures, the user can perform the actions described in "Surgical Training and Planning" without physically touching the touch screen. This allows more of the object to be visualized on the interface screen, such that the user themself does not obscure their view of the data. In one example embodiment, three-dimensional surgical plan data associated with a surgical plan may be provided and rendered on the display of the mobile computing device, such that a relative orientation of the three-dimensional surgical plan data and the three-dimensional image data is preserved when rendering the image of the surgical plan.

Figure 18A:
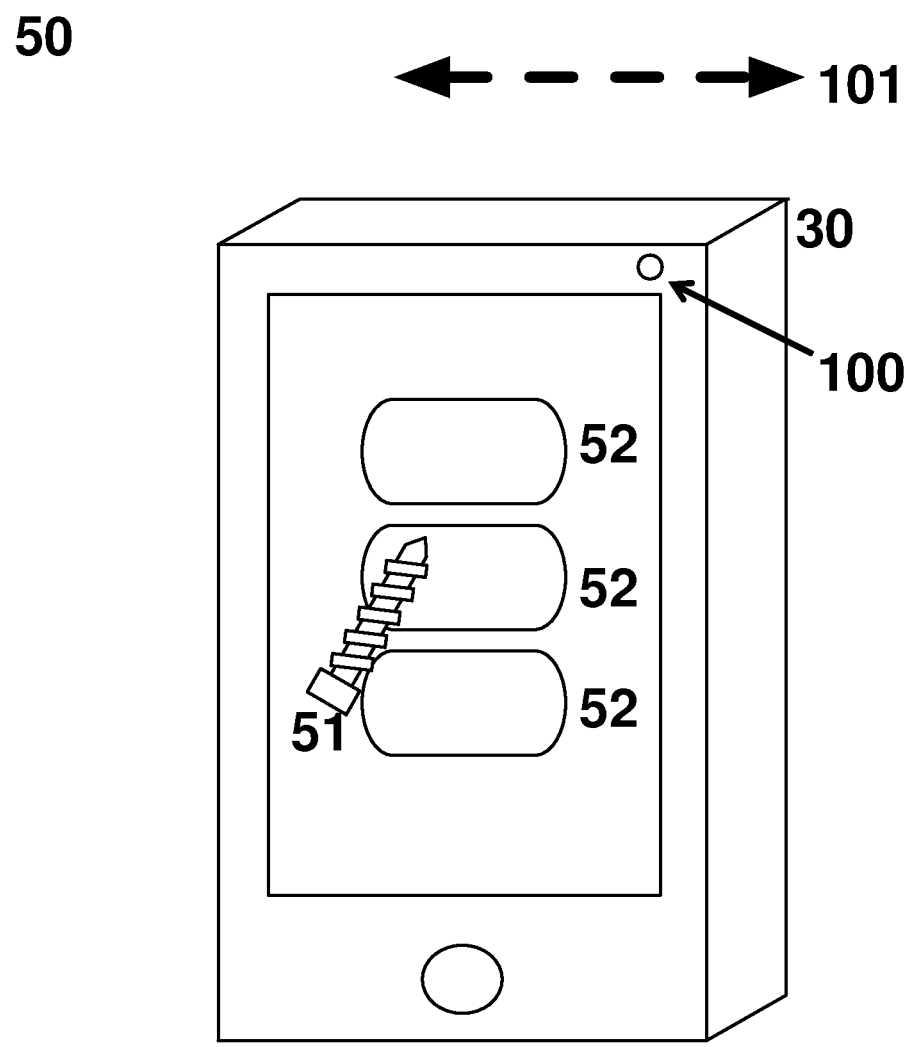
FIG. 18a is an example of object manipulation and screw placement through gesture-based control using a front-facing camera on the mobile computing device.
Figure 18B:
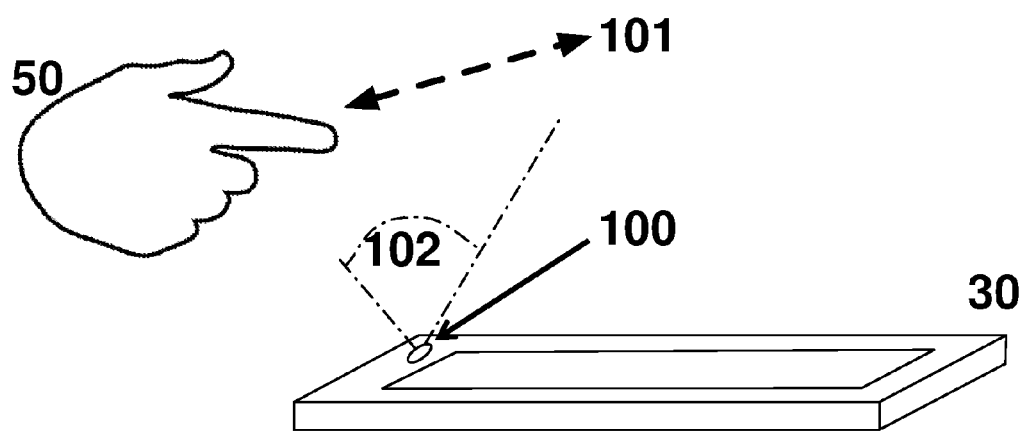
FIG. 18b is an alternate viewpoint of user interaction through gestures using a front-facing camera on the mobile computing device.

FIG. 18a presents an example of the aforementioned touchless gesture identification method. It is functionally similar to the embodiment described in FIG. 12, however, rather than the user 50 interacting with a touch-sensitive screen, the user instead motions a finger over 101 the mobile computing device's front-facing camera 100. Another view is show in FIG. 18b. As long as the hand is kept above the mobile computing device 30 in such a position that it remains in the front-facing camera's 100 field of view 102. Provided that this condition is met, any motion 101 can be translated into a mobile computing device input coordinate 60. This could also be accomplished via cameras that are on the back of the mobile computing device or with cameras that are physically separated from the mobile computing device, where camera to mobile computing device communication could occur, but is not limited to, a physical wired connection or wireless connection.

Figure 19:
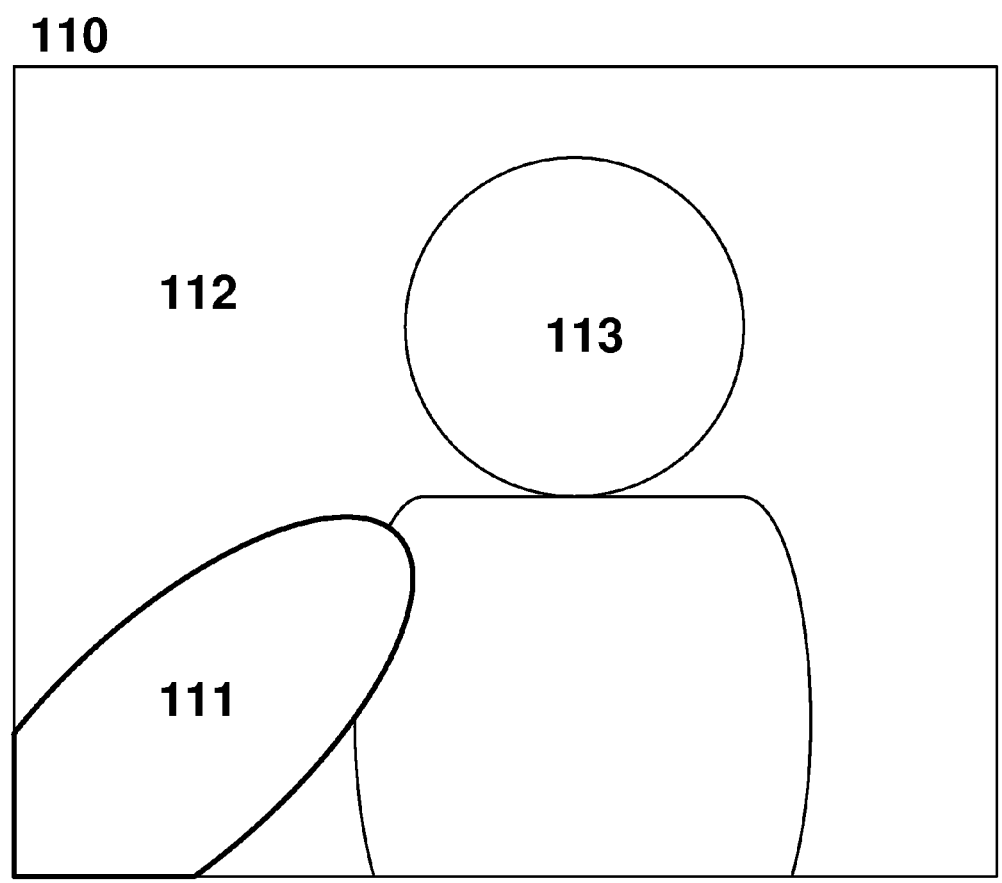
FIG. 19 is an example of what is seen by the front-facing camera when used for gesture-based input.

FIG. 19 shows the view 110, as seen by the camera 100. Due to how the mobile computing device is generally held, the camera will see the thumb or finger 111, along with the user themselves 113. It is assumed that the background 112 is static to simplify obtaining the input. The input process does not directly map the observed position of the thumb or finger 111 to a position $\overline{x}=(x, y)$ on the image. Rather, it determines the change in input position $\overline{\Delta x}=(\Delta x, \Delta y)$. This avoids any potential problems when tracking of the appendage is lost, such as when it moves out of the camera's field of view. Should such an error be detected, the input is left unmodified. This also expands the number of possible interactions available to the user so that along with the ability to manipulate the data through orientation, they may perform similar actions through gesture.

Figure 20:
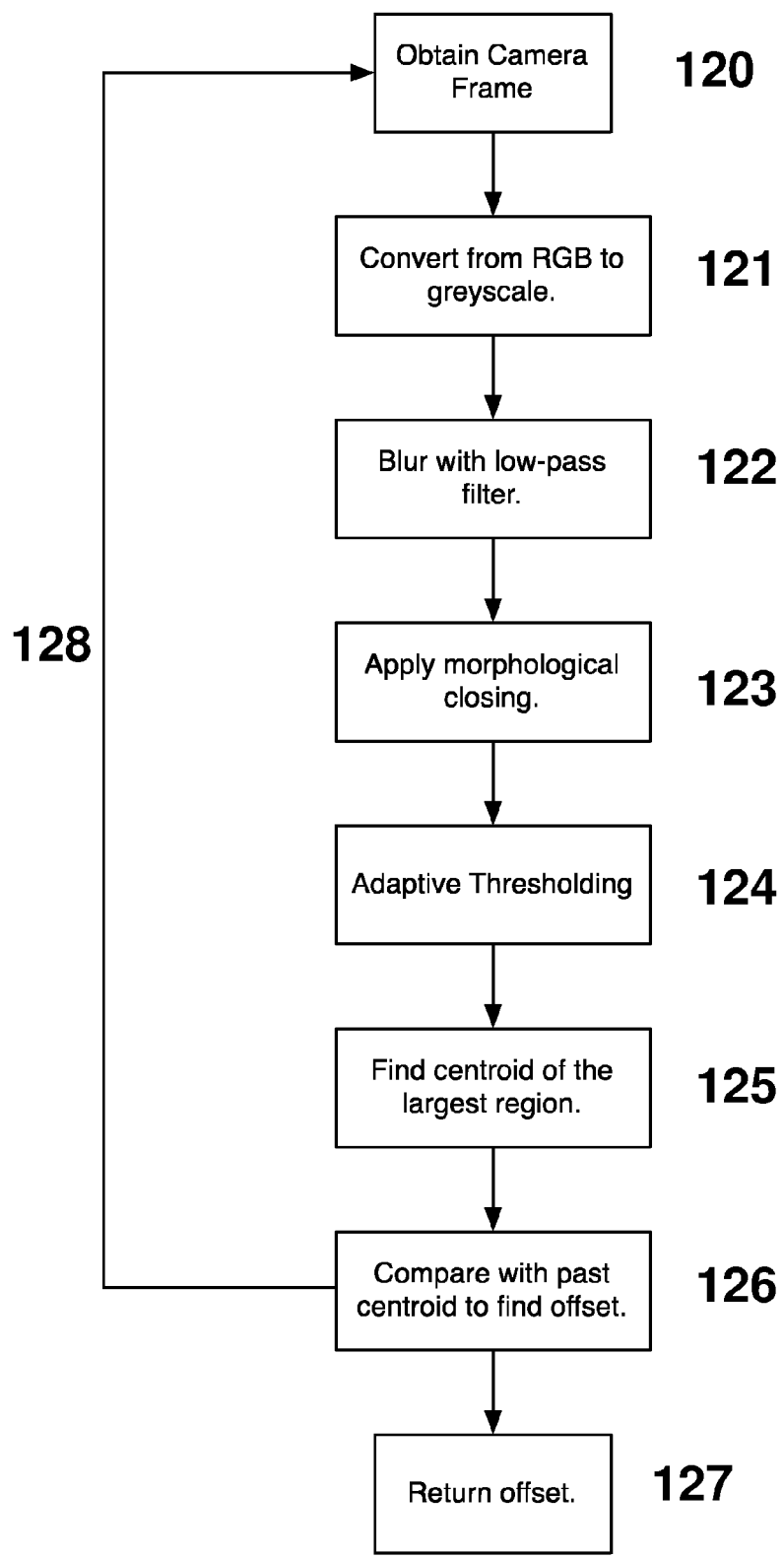
FIG. 20 is a flowchart describing the algorithm used to transform the information captured by the camera into a horizontal and vertical offset value that is used directly by the mobile computing device as an input.

The process of obtaining $\overline{\Delta x}$ is described in FIG. 20. First a full-colour RGB (red-green-blue) image is obtained 120 from the front-facing camera 100. The image is then converted from colour to intensity 121 such that each pixel only assumes one value. In one embodiment, the pixel values are integers on the range of $0 \leq I \leq 255$ where in another embodiment the pixel values are real numbers on the range of $0.0 \leq I \leq 1.0$. The image is blurred with a low-pass filter 122 to remove noise. In one embodiment, this may be a Gaussian low-pass filter. After blurring a morphological closing is applied 123 to only retain large-scale structure in the image. A threshold value is chosen 124 by examining the statistics of the image and choosing a value T such that for any pixel I(x,y) in the image a new image is created where I'(x,y)=0 if I(x,y)<T and I'(x,y)=1 if I(x,y)≥T. The centroid of the largest region in the new image is found 125 and compared with the previous centroid 126 to generate an offset 127. The offset value is used to directly modify the position and orientation of the anatomical object. This process is repeated 128 each time an image is captured by the front-facing camera 100 to direct the manipulation of the virtual object, such as the spine.

The proposed tracking method is only one such method for gestural input. Other methods could also be used to obtain the position of the thumb or other fingers in a similar manner. In one embodiment, optical flow is used to estimate the motion of pixels over time such the moving objects, such as the thumb, are separating from stationary objects, such as the background. In another embodiment texture and edge information are used to estimate what pixels in the image constitute the background and what pixels constitute the thumb as, to the camera, the thumb appears as a feature-less dark area. In another embodiment, machine-identifiable markets, such as coloured stickers, may be applied to one or more fingers of the user's hand for tracking purposes. Alternatively, image-based foreground/background segmentation may be employed to determine the location of a user's thumb or finger. In other embodiments, feature point tracking or template tracking (in which fiducial markers would be utilized) may be employed. The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Therefore what is claimed is:

1. A computer implemented method of dynamically displaying an anatomical object on a mobile computing device, the mobile computing device including sensors for determining an orientation of the mobile computing device and a display for displaying the anatomical object, the method comprising the steps of:
   a) obtaining three-dimensional image data associated with the anatomical object;
   b) determining a virtual camera vector defining a distance between a virtual camera and the anatomical object upon rendering of the anatomical object;
   c) determining a reference vector associated with the anatomical object, such that when rendering the anatomical object on the display, the reference vector is aligned with a gravity vector when the mobile computing device is oriented in a reference orientation;
   d) interrogating the sensors of the mobile computing device and determining an orientation of the mobile computing device;
   e) determining a transformation such that the reference vector is aligned with the gravity vector, and such that the anatomical object is perceived as residing within the display at a location corresponding to the virtual camera vector;
   f) applying the transformation to three-dimensional image data and obtaining transformed three-dimensional image data such that when rendered on the display, the anatomical object image appears to be stationary after a change in the orientation of the mobile computing device; and
   g) rendering an image of the anatomical object on the display of the mobile computing device according to the transformed three-dimensional image data.

2. The method according to claim 1 further comprising the step of repeating steps d) to g) one or more times.

3. The method according to claim 1 further wherein the transformation is an affine transformation.

4. The method according to claim 1 wherein the transformation is an affine transformation.

5. The method according to claim 1 wherein the transformation is a net transformation, and wherein the step of determining the net transformation comprises the steps of:
   determining an orientational transformation such that the reference vector is aligned with the gravity vector; and
   determining a translational transformation such that the anatomical object is perceived as residing within the display at a location corresponding to the virtual camera vector.

6. The method according to claim 1 wherein the reference vector associated with the anatomical object is selected such that the reference vector is aligned with the gravity vector when the display is positioned in a horizontal orientation.

7. The method according to claim 1 wherein the three-dimensional image data is provided as a mesh.

8. The method according to claim 7 wherein the transformation is applied to each point in the mesh.

9. The method according to claim 1 further comprising the steps of:
   receiving additional three-dimensional image data associated with a surgical device to be inserted into the anatomical object;
   determining an initial position and an initial orientation of the surgical device relative to that of the anatomical object, thereby establishing an initial relative position of the surgical device;
   rendering an image of the surgical device on the display in accordance with the initial relative position.

10. The method according to claim 9 wherein the initial position is associated with a pre-selected point of entry for the surgical device to enter the anatomical object.

11. The method according to claim 10 wherein the anatomical object includes a bone structure, and surgical device is a screw.

12. The method according to claim 9 wherein the surgical device is positioned by the steps of:
   receiving input defining a translation of the surgical device; and
   generating an additional transformation associated with the translation;
   employing the additional transformation to determine an updated relative position of the surgical device; and
   rendering an updated image of the surgical device on the display in accordance with the updated relative position.

13. The method according to claim 12 wherein the step of receiving the input includes the steps of:
   detecting a touchless gesture; and
   inferring the translation based on the touchless gesture.

14. The method according to claim 12 further comprising the steps of:
   obtaining boundary three-dimensional image data defining a forbidden region for insertion of the surgical device;
   determining whether or not the updated relative position of the surgical device is within the forbidden region.

15. The method according to claim 14 wherein in the event that a portion of the surgical device is determined to lie within the forbidden region, notifying the user.

16. The method according to claim 14 further comprising the steps of:
   receiving placement information identifying one or more suitable locations for placement of the surgical device;
   determining an accuracy of the placement of the surgical device by comparing the updated relative position of the surgical device with the placement information.

17. The method according to claim 16 further comprising providing feedback associated with the accuracy of the placement of the surgical device.

18. The method according to claim 1 further comprising the steps of:
   receiving three-dimensional surgical plan data associated with a surgical plan;
   rendering an image of the surgical plan on the display;
   wherein a relative orientation of the three-dimensional surgical plan data and the three-dimensional image data is preserved when rendering the image of the surgical plan.

19. A computer implemented method of dynamically displaying an anatomical object on a mobile computing device, the mobile computing device including sensors for determining an orientation of the mobile computing device and a display for displaying the anatomical object, the method comprising the steps of:
   a) obtaining three-dimensional image data associated with the anatomical object;
   b) interrogating the sensors of the mobile computing device and determining a change in an orientation of the mobile computing device;
   c) rendering an image of the anatomical object on the display, such that the anatomical object image appears to be stationary after the change in the orientation of the mobile computing device.

20. The method according to claim 19 further comprising the step of repeating steps b) and c) one or more times.

21. A non-transitory computer-readable storage medium comprising instructions for dynamically displaying an anatomical object on a mobile computing device, the mobile computing device including sensors for determining an orientation of the mobile computing device and a display for displaying the anatomical object, wherein execution of the instructions by one or more processors causes the one or more processors to carry out the steps of:
   a) obtaining three-dimensional image data associated with the anatomical object;
   b) determining a virtual camera vector defining a distance between a virtual camera and the anatomical object upon rendering of the anatomical object;
   c) determining a reference vector associated with the anatomical object, such that when rendering the anatomical object on the display, the reference vector is aligned with a gravity vector when the mobile computing device is oriented in a reference orientation;
   d) interrogating the sensors of the mobile computing device and determining an orientation of the mobile computing device;
   e) determining a transformation such that the reference vector is aligned with the gravity vector, and such that the anatomical object is perceived as residing within the display at a location corresponding to the virtual camera vector;
   f) applying the transformation to three-dimensional image data and obtaining transformed three-dimensional image data such that when rendered on the display, the anatomical object image appears to be stationary after a change in the orientation of the mobile computing device; and
   g) rendering an image of the anatomical object on the display of the mobile computing device according to the transformed three-dimensional image data.

* * * * *